United States Patent
Crocco et al.

(10) Patent No.: US 11,612,381 B2
(45) Date of Patent: Mar. 28, 2023

(54) METHOD FOR TISSUE CHARACTERIZATION BY ULTRASOUND WAVE ATTENUATION MEASUREMENTS AND ULTRASOUND SYSTEM FOR TISSUE CHARACTERIZATION

(71) Applicant: ESAOTE S.p.A, Genoa (IT)

(72) Inventors: Marco Crocco, Ovada (IT); Stefano De Beni, Genoa (IT)

(73) Assignee: Esaote S.p.A., Genoa (IT)

( * ) Notice: Subject to any disclaimer, the term of this patent is extended or adjusted under 35 U.S.C. 154(b) by 188 days.

(21) Appl. No.: 16/935,311

(22) Filed: Jul. 22, 2020

(65) Prior Publication Data

US 2021/0022710 A1    Jan. 28, 2021

(30) Foreign Application Priority Data

Jul. 25, 2019   (EP) .................................... 19188283

(51) Int. Cl.
*A61B 8/08*  (2006.01)
*A61B 8/14*  (2006.01)
(Continued)

(52) U.S. Cl.
CPC .............. *A61B 8/485* (2013.01); *A61B 8/145* (2013.01); *A61B 8/461* (2013.01); *A61B 8/5207* (2013.01);
(Continued)

(58) Field of Classification Search
CPC ......... A61B 8/485; A61B 8/145; A61B 8/461; A61B 8/5207; A61B 8/5246;
(Continued)

(56) References Cited

U.S. PATENT DOCUMENTS

| 5,606,971 A | 3/1997 | Sarvazyan |
| 2010/0249590 A1 | 9/2010 | Kanayama et al. |

(Continued)

FOREIGN PATENT DOCUMENTS

| JP | H03-024868 B2 | 4/1991 | |
| JP | 2017104526 A * | 6/2017 | ............... A61B 8/08 |
| WO | 2016108178 A1 | 7/2016 | |

OTHER PUBLICATIONS

Extended European Search Report dated Jan. 3, 2020, which issued in corresponding EP Patent Application No. EP19188283.6.

*Primary Examiner* — Joel Lamprecht
*Assistant Examiner* — Ashish S Jasani
(74) *Attorney, Agent, or Firm* — Dickinson Wright PLLC

(57) ABSTRACT

A method for tissue characterization by ultrasound wave attenuation measurements is provided that comprises:
a) transmitting at least an ultrasound pulse in a target body;
b) receiving ultrasound pulses reflected by the target body and transforming the reflected ultrasound pulses into RF reception signals;
c) extracting an envelope of the received RF signals;
d) carrying out a logarithmic compression of the extracted envelope and
e) computing a propagation depth dependent attenuation coefficient of the tissues crossed by the ultrasound pulse in the target body as the slope of the line fitting the logarithmic compressed envelope data along the penetration depth of the ultrasound pulse in the target body.

The disclosure relates also to an ultrasound system for carrying out the method.

12 Claims, 11 Drawing Sheets

(51) Int. Cl.
*A61B 8/00* (2006.01)
*G01S 7/52* (2006.01)
*G01S 15/89* (2006.01)

(52) U.S. Cl.
CPC ........ *A61B 8/5246* (2013.01); *G01S 7/52022* (2013.01); *G01S 7/52053* (2013.01); *G01S 15/8954* (2013.01)

(58) Field of Classification Search
CPC .............. A61B 8/5223; G01S 7/52022; G01S 7/52053; G01S 15/8954; G01S 7/52036; G01S 7/52042; G01S 7/52071; G01S 15/8915
See application file for complete search history.

(56) References Cited

U.S. PATENT DOCUMENTS

| | | | |
|---|---|---|---|
| 2010/0317971 A1* | 12/2010 | Fan | G01S 15/8993 600/439 |
| 2014/0018679 A1* | 1/2014 | Chen | A61B 8/48 600/438 |
| 2014/0114189 A1 | 4/2014 | Kanayama et al. | |
| 2018/0014814 A1* | 1/2018 | Labyed | G16H 50/30 |
| 2019/0029649 A1* | 1/2019 | Tanigawa | A61B 8/5223 |
| 2019/0125308 A1* | 5/2019 | Rosenzweig | A61B 8/5207 |
| 2019/0254634 A1* | 8/2019 | Honjo | G01S 7/52073 |
| 2019/0282209 A1* | 9/2019 | Xie | G01S 7/52042 |
| 2019/0298312 A1* | 10/2019 | Labyed | A61B 8/5269 |
| 2019/0350558 A1* | 11/2019 | Labyed | G16H 50/30 |

* cited by examiner

METHOD FOR TISSUE CHARACTERIZATION BY ULTRASOUND WAVE ATTENUATION MEASUREMENTS AND ULTRASOUND SYSTEM FOR TISSUE CHARACTERIZATION

BACKGROUND

Field

The present invention relates to a method for tissue characterization by ultrasound wave attenuation measurements, the said method comprising the steps of a) transmitting at least an ultrasound pulse in a target body;

b) receiving the ultrasound waves reflected by the said target body and transforming the said reflected ultrasound pulses in RF reception signals and computing the propagation depth dependent attenuation coefficient of the tissues crossed by the ultrasound pulse in the target body as a function of the said RF reception signals.

Related Art

Attenuation in ultrasound is the reduction in amplitude of the ultrasound beam as a function of distance through the imaging medium. As the ultrasound beam travels through the body it loses energy. The intensity and amplitude of the sound wave decreases, and this process is known as attenuation. Attenuation coefficients are used to quantify different media according to how strongly the transmitted ultrasound amplitude decreases as a function of frequency. The amount of attenuation that occurs will depend on the type of tissue the sound wave is traveling through. Where the molecules of the tissue are densely packed (such as bone), attenuation will be much greater than in less densely packed tissue (such as fat). Different tissues have different attenuation coefficients depending on the amount of attenuation occurring in the beam of sound. The attenuation coefficient (a) can be used to determine total attenuation in dB in the medium. Attenuation is linearly dependent on the medium length and attenuation coefficient, and also on the frequency of the incident ultrasound beam for biological tissue. The higher the frequency, the greater the amount of attenuation that will occur in any given tissue. Attenuation coefficients vary widely for different media. In biomedical ultrasound imaging however, biological materials and water are the most commonly used media. Attenuation will occur not only in the beam of sound produced by the transducer as it propagates through tissue, but also in the returning echoes as they travel back to the transducer.

Absorption is the main factor causing attenuation of the ultrasound beam. The higher the frequency of the sound wave, the greater the amount of absorption that will occur. Energy is transferred from the sound wave into the medium through which it is traveling.

Ultrasound attenuation parameters are gaining increasing clinical importance. In particular in relation to steatosis. Steatosis is the most frequent liver disease, with both alcoholic (ALFD) and nonalcoholic (NALFD) etiology. NALFD affects up to 30% of adult western population. If not treated liver steatosis can lead to more severe illness such as fibrosis, cirrhosis and liver cancer. Liver steatosis is mainly symptomless, therefore patients are not motivated to undergo liver biopsy. Tissue attenuation is a parameter strongly correlated with liver fat content. Attenuation measurement and imaging by medical ultrasound can provide a powerful, not-invasive, diagnostic tool for liver steatosis staging.

Different methods for carrying out measurements of attenuation coefficients in tissues are known.

Document Jpn. Pat. Appln. KOKAI Publication No. 3-24868 discloses a technique of divisionally transmitting and receiving ultrasonic pulses in different frequency bands twice in the same direction. Based on the fact that the tissue attenuation amount varies depending on the frequency, this technique infers the attenuation constant of a medium by comparing the attenuation amounts of two pulses. Jpn. Pat. Appln. KOKAI Publication No. 3-24868 also discloses a technique of adding attenuation information to a conventional tomogram by extracting two different frequency band components contained in a reception signal upon performing transmission/reception once in the same direction, and weighting and adding the respective signals. This technique can be easily implemented by one transmission/reception cycle.

Document US20100249590 discloses an ultrasonic diagnostic apparatus comprising: a transmission unit which transmits a composite ultrasonic wave obtained by combining at least a first ultrasonic wave having a first center frequency with a second ultrasonic wave having a second center frequency different from the first center frequency at least twice in each of a plurality of directions in an object while modulating a phase; an ultrasonic reception unit which receives, from the object, an echo signal corresponding to each of the at least two transmissions in each of the plurality of directions; a signal extraction unit which extracts a first echo signal corresponding to the first ultrasonic wave and a second echo signal corresponding to the second ultrasonic wave after canceling out harmonics by performing subtraction processing between the echo signals respectively corresponding to the at least two transmissions in each of the plurality of directions; and an image generating unit which generates an attenuation image representing attenuation of an ultrasonic wave propagating in the object by using the first echo signal and the second echo signal.

US2014114189 discloses a method for estimating the amount of attenuation by calculating the signal intensity of a received signal. Several conventional methods are disclosed therein. One of these methods provides for estimating the amount of attenuation specific to a subject by transmitting multiple ultrasound pulses each having a different center frequency and by comparing the received signals that are acquired with regards to how much the intensity of the received signals changes in the depth direction. Another method disclosed therein comprises the steps of comparing multiple frequency signals with regards to the change in their intensity and utilizing the characteristic that the amount of attenuation of ultrasound waves in a living body depends on the frequency.

SUMMARY

Example embodiments of the present invention aim to provide for a method and a system for tissue characterization by ultrasound wave attenuation measurements improving the drawbacks of the method according to the state of the art.

According to a first aspect of the present invention, a method for tissue characterization by ultrasound wave attenuation measurements is provided, the said method comprising the steps of a) transmitting at least an ultrasound pulse in a target body;

b) receiving the ultrasound pulses reflected by the said target body and transforming the said reflected ultrasound pulses in RF reception signals;

c) extracting the envelope of the received RF signals;

d) carrying out a logarithmic compression of the said extracted envelope and e) computing the propagation depth dependent attenuation coefficient of the tissues crossed by the ultrasound pulse in the target body as the slope of the line fitting the said logarithmic compressed envelope data along the penetration depth of the ultrasound pulse in the said target body.

In an embodiment the transmitted ultrasound pulse is a wide-frequency band pulse or a multifrequency pulse comprising frequency components with frequencies within a predetermined frequency band, the step of determining RF signal components with frequencies within a sub range of the predetermined frequency band by filter-bank filtering is carried out before the step c) of extracting the envelope of the RF reception signal, the said envelope extraction being carried out separately for each frequency sub-band component of the RF reception signal, the said step d) of logarithmic extraction and the said step e) being carried out attenuation coefficient for each frequency sub-band component of the RF reception signal, f) for each propagation depth of the ultrasound pulse the attenuation coefficient being determined as the mean or median value of the attenuation coefficients calculated for each frequency sub-band component of the RF reception signal.

According to a further embodiment, a sequence of several ultrasound pulses is transmitted into the target body and a sequence of reception signals is acquired from the sequence of the reflected ultrasound pulses, the said steps c) to e) and optionally the step f) being carried out for each of the reception signals of the sequence of reception signals and g) the attenuation coefficient at a propagation depth is computed as the mean or the median value of the attenuation coefficients at the said penetration depth of the attenuation coefficients computed from each of the reception signals of the sequence of reception signals.

The envelope of the RF reception signals may be expressed by the following equation:

$$s(f,z) = \exp(-\alpha f z)\mathrm{scat}(f,z)$$

In which
s(f,z) is the frequency and depth dependent envelope of the RF reception signal;
Exp($-\alpha f z$) is the attenuation term
$\alpha$ is the slope of a line fitting the logarithm of the data envelope;
f is the frequency;
z is the propagation depth of the ultrasound pulse;
scat(f,z) is a function describing the speckle.
Compressing the above envelope by a logarithmic compression, is described by the following equation:

$$\ln(s(f,z)) = -\alpha f z + \ln(\mathrm{scat}(f,z))$$

According to a further aspect the invention aims to overcome the drawbacks of low signal to noise ratio regions or losses in signal to noise ratio.

According to an embodiment, in the case the at least one ultrasound pulse transmitted into the target body is a wide frequency pulse which is filtered in reception of the reflected pulses by a filter-bank, the loss in signal to Noise Ratio is compensated by repeating the transmission of the said ultrasound pulse and combining the receipt signals generated by the corresponding reflected pulses.

According to a variant embodiment, different signal parameters may be used for estimating the attenuation coefficient such as one or more of the parameters listed in the following list:

Signal intensity, spectral shape of the received signals, out of range attenuation slope along the propagation depth.

DETAILED DESCRIPTION OF EXAMPLE EMBODIMENTS

Figure 1:
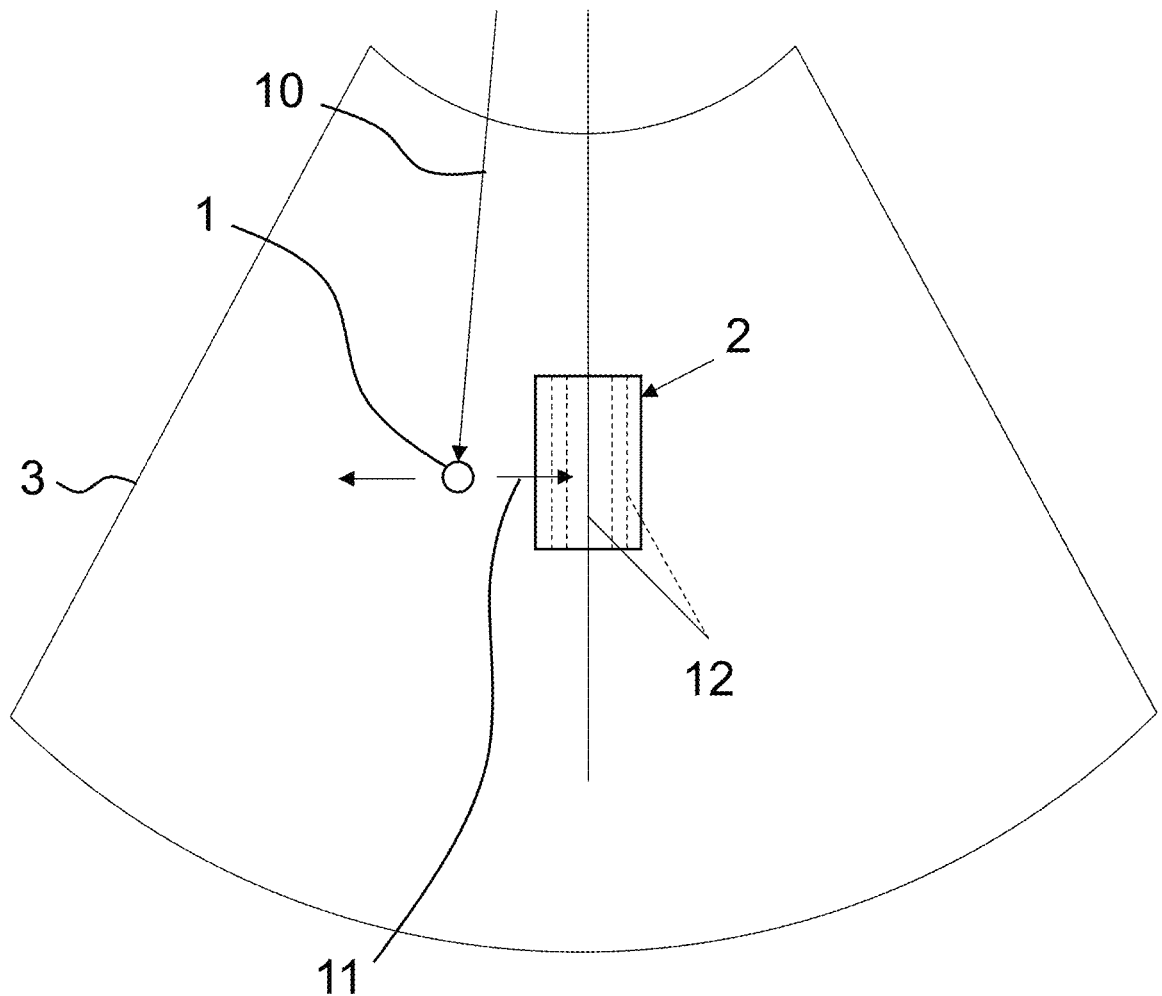
FIG. 1 is a schematic view of a ROI in a target object within which the attenuation parameters and or the elasticity parameters at different focal points along different scan lines and at different depths has to be measured with one of the embodiments according to the present invention.

Elasticity of soft biological tissues has been used for evaluating possible pathological conditions since the dawning of medicine. The use of manual palpations for evaluating the health condition of the tissues is still used commonly in routine medical examinations. For example the presence of rigid masses found during routine breast examinations is often an early indication of breast cancer. Manual palpation methods however are relatively little objective and are limited to surface anatomical structures.

The methods for quantifying the elasticity or for the comparative measurement of biological tissues by ultrasounds allow deep-tissue elasticity to be measured in the body under examination, are reliable and therefore are used in clinical practice.

Unlike the traditional ultrasound imaging, such as for example B-mode, that allows images to be acquired where tissues with different acoustic properties are distinguished, the methods measuring the elasticity allow tissues with different mechanical properties to be distinguished. To do this, such methods carry out an excitation of the tissues and monitor the strain response, which is related to tissue elasticity.

A type of elasticity measurement methods provides to use transverse waves, or shear waves, generated after an excitation, and are defined as Shear Wave Elasticity Imaging (SWEI). These methods provide to generate shear waves in the tissue following an acoustic disturbance, called as shock disturbance, of the first excitation point applied by the ultrasound probe, and consequently to monitor the shear waves in the regions of interest placed outside the area or the point of excitation. By measuring the displacements over time of the image or of the pixels of the image or of the pixels of a Line of Sight at a plurality of lateral positions separated by a known distance from the excitation source, it is possible to estimate the shear wave speed.

Actually the measurement is indirect since the method detects the propagation speed of the shear wave in a direction substantially orthogonal to the acoustic shock disturbance of the excitation point.

The relation between speed of such shear wave and the elasticity is approximate and it depends on some assumptions about the density of the tissue under examination.

The tissue elasticity is proportional to the propagation speed ρ of the shear wave $V_s$, according to the following formula:

$$E \approx 3\rho V_s^2$$

wherein it is assumed that p", namely that tissue density is unit quantity.

The document U.S. Pat. No. 5,606,971 describes a SWE method, that uses a focused ultrasound transducer which induces shear waves in a tissue by sending modulated ultrasonic pulses. The shear wave of the frequency of the modulating signal is detected. The mechanical properties of tissues under examination are evaluated on the basis of the measured values of speed and attenuation of shear waves.

A subset of such methods is the one defined as pSWE (Point Shear Wave Elasticity), where, instead of an image, a point measurement generally averaged in the region of interest is generated.

A problem of the known methods derives from the possibility of the probe and/or patient moving during the examination. Such movements during acquisition can be substantially considered of two different types: transversal, i.e. along the direction of propagation of the transversal wave, due, for example, to a translation or shift of the probe on skin of the patient or a rotation of the probe by small angles on the plane of the image or longitudinal, i.e. along the direction of propagation of the ultrasound beam, caused, for example, by a different relative position of the probe with reference to the patient due to a different pressure of the hand holding the probe or patient breathing.

In both cases the measurement is altered: in presence of a transversal movement the wave is detected slightly beforehand or slightly later, depending on the direction of rotation or of translation of the probe; in presence of a longitudinal movement the reconstructed signal contains also the effect of such movement consisting in an erroneous ramp trend superimposed on the wave. This leads to a calculation of the shear wave propagation speed not corresponding to reality, and therefore to a distorted estimation of tissue elasticity.

A further method for carrying out elasticity measurements is described in WO2016108178. According to this method the elasticity parameter is measured by estimating the velocity of a shear wave according to a sequence of reference ultrasound pulses transmitted in a target body followed by a shock wave for generating the shear wave and then the displacements of the reflectors is measured by a sequence of tracking ultrasound pulses which are transmitted focused along lines which are laterally staggered one form the other with reference to the origin of the shear wave.

The method disclosed in WO2016108178 therefore allows a reliable measurement of the elasticity of the material under examination to be obtained, particularly of the biological tissues under examination, by correcting anomalies due to the movement, in particular due to the mutual rotation of the probe with respect to the patient or vice versa on the image plane. The fact of providing two excitation points on two opposite sides of the region of interest, allows movement errors to be compensated since, if the detection of the shear wave is anticipated for the measurement corresponding to the first excitation point, it is delayed for the measurement corresponding to the second excitation point and vice versa. This is obviously valid for movements of the probe and/or of the patient that are small and always having the same direction during the examination.

The method disclosed in the above document allows to carry out the measurement of the elasticity of any biological tissue involved by the cardiac movement, and it is particularly advantageous in relation to the measurement on the liver.

Tissue elasticity and tissue ultrasound attenuation may provide complementary diagnostic information about correlated diseases. For example, liver fibrosis is often occurring together with liver steatosis.

Standard medical ultrasound devices provide elasticity and attenuation imaging modalities where B-mode is overlapped to a color-coded measurement map. The two imaging modalities are separate modalities and need to perform two separate examination. This causes additional time, cost and patient discomfort also considering that the patient is many times is not collaborative.

According to a further aspect of the present invention, the method for tissue characterization by ultrasound wave attenuation measurements is provided in combination with the steps of estimating shear wave velocity coefficient.

According to an embodiment, the said combined method for tissue characterization and elasticity measurements by ultrasound comprises the following steps:

a1) acquiring an ultrasound image (3);

b1) defining a region of interest (2) in the image (3), the region of interest including image pixels;

transmitting an acoustic disturbance ultrasound beam (10) directed at an excitation point (1), the acoustic disturbance ultrasound beam configured to produce a shear wave (11) that has a direction of propagation extending laterally from a direction of propagation of the acoustic disturbance ultrasound beam (10);

c1) measuring displacements of the image pixels induced by the shear wave (11) by transmitting a sequence of ultrasound tracking pulses which are laterally staggered at different lateral positions relatively to the said excitation point and receiving the corresponding reception signals;

d1) assessing the propagation speed of the shear wave in the direction of the lateral displacement of the tracking pulses and/or the stiffness value of tissue in the region of interest (2) based on the displacements measured at step c1).

at least some of the reception signals generated by the reflection of the one or more of the said tracking pulses being as reception signals for computing the attenuation coefficient at predetermined propagation depths.

at least some of the tracking pulses are transmitted at least twice, the received signals due to the reflected pulse of one of the at least two transmitted tracking pulses being used for computing the shear wave velocity while the received signals due to the reflected pulse of the second of the at least two transmitted tracking pulses being used for computing the attenuation coefficient.

According to a further embodiment, before transmitting the shear wave generating pulse or the shear wave generating pulses at least one or a sequence of ultrasound reference pulses is transmitted in the region of interest (2) defined at step b1), at least some of the reception signals generated by the reflection of the one or more of the said reference pulses being used as reception signals for computing the attenuation coefficient at predetermined propagation depths.

According to still a further embodiment, at least some of the reference pulses are transmitted at least twice, the received signals due to the reflected pulse of one of the at least two transmitted reference pulses being used for computing the shear wave velocity while the received signals due to the reflected pulse of the second of the at least two transmitted reference pulses being used for computing the attenuation coefficient.

Thanks to the above embodiments, both the attenuation and the elasticity maps are obtained with a single examination.

The two possible alternative embodiments providing two transmit-receive sequences carried out in sequence one for determining the elasticity parameters and the other for determining the attenuation coefficients or providing only one transmit-receive sequence which is used for both modalities, namely for determining the elasticity parameters and for determining the attenuation coefficients, may be implemented as a choice in combination.

A user interface may allow the operator to select one of these two alternative embodiments and to start the selected one.

FIG. 1 shows the interface of the method according to the present invention, which interface shows a B-mode ultrasound image 3. On the B-mode image 3 the user defines a region of interest 2 through a gate, in which region of interest the attenuation coefficients of the tissue have to be measured.

The region of interest 2 may have any shape, preferably a rectangular shape or as a section of an annulus, and preferably it has a predetermined size for the end user. The user can place the region of interest 2 where he/she desires, preferably only in one portion of the image defined in the development step, such to avoid areas not suitable for the measurement, such as for example areas of the image that are too deep or too superficial.

During the dedicated acquisition, the B-mode image is still, or "frozen", and it can be removed from such condition only after producing the numerical result.

According to a variant embodiment the B-mode data acquisition is interleaved with the acquisition of the data for determining elasticity and for determining the attenuation parameters. Thanks to this variant embodiment data stream of B-mode image data and elasticity and attenuation data are acquired and the elasticity data and the attenuation data are refreshed in real time with the B-mode image data.

Therefore the user, once defining the region of interest 2, starts the measurement; the image is made as still, and the special insonification/acquisition is carried out for estimating the shear wave. Once such step has ended, the data are processed and the obtained result is displayed on the monitor.

Once a measurement has ended, the image can be "unfrozen" such to allow a new shot and a new acquisition, till leaving the mode.

Once the region of interest 2 is defined.

One or more ultrasound pulses or one or more sequences of ultrasound pulses are transmitted in the ROI 2 of the target body along at least one scan line 12. In the present example several scanlines which are laterally staggered one from the other are provided and along each one of which scanlines at least an ultrasound pulse or a sequence of ultrasound pulses is transmitted in the ROI 2.

The ultrasound pulse is focused along the corresponding scan line 12 at different positions corresponding to different depth of propagation of the pulse inside the body.

The reflected pulses are then collected and transformed by the transducer of a probe in RF reception signals.

According to the present method the envelope of the RF reception signals is generated.

Equation (1) describes the said envelope $$s(f,z) = \exp(-\alpha f z) \text{scat}(f,z)$$

In this equation $s(f,z)$ is the frequency and depth dependent envelope of the RF reception signal;

$\exp(-\alpha f z)$ is the attenuation term $\alpha$ is the slope of a line fitting the logarithm of the data envelope;

f is the frequency;

z is the propagation depth of the ultrasound pulse;

$\text{scat}(f,z)$ is a function describing the speckle.

Equation (2) describes the logarithmic compression of the envelope:

$$\ln(s(f,z)) = -\alpha f z + \ln(\text{scat}(f,z))$$

Here the term a represents the slope of the line fitting the envelope at a certain depth range.

To improve robustness, attenuation can be computed over multiple frequency bands taking the mean or median value of the attenuation parameters computed at a certain depth range for each of two or more frequency sub bands of the multiple frequency band.

Figure 3:
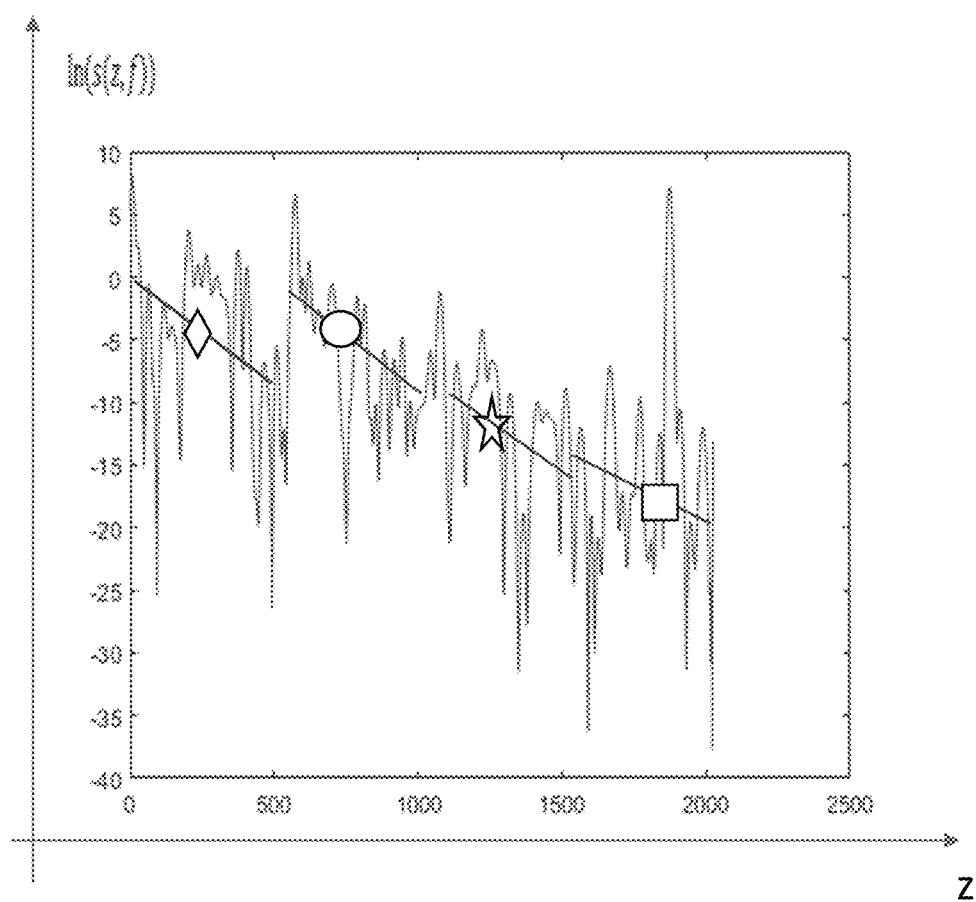
FIG. 3 shows the graphic representation of the mathematical model for determining the attenuation parameter at different depths along a scan line while the line fitting the logarithmic compressed envelope of the RF reception signals at different depth ranges are shown.

FIG. 3 is an example showing the envelope function at different depths z and the line fitting the said envelope for each of four depth ranges.

At the different depth ranges corresponding or centered at the different focal points along the scan corresponding scan line 12 the logarithm of the envelope is approximated by fitting the data with a linear function. The attenuation of the tissue at the said depth range is computed as the slope of the said linear function.

The above attenuation imaging can be combined with a tissue elasticity imaging.

In this case a first excitation point 1 is defined within the acquired B-mode image 3.

For carrying out the measurements of the elasticity parameters of the tissue in the region of interest (ROI) a focused ultrasonic beam 10 is generated for the acoustic disturbance of one target point 1, to generate a shear wave 11. The shear wave 11 originates in the first excitation point 1 and has a propagation direction substantially perpendicular to the direction of propagation of the ultrasonic beam 10, in the two opposite departing directions denoted by the arrows in the figure. The first excitation point 1 is placed such that the shear wave 11 passes through the region of interest 2.

The generated shear wave 11 is measured at a plurality of lines of sight placed inside the region of interest 2 at different predetermined distances from the first excitation point 1. The figure shows the line of sight under examination, while the other lines of sight are broken lines.

By the measurement of the passage of the shear wave on all the lines of sight the propagation speed of the measured shear wave is calculated.

As it will be described with further details in the following description with reference to FIG. 4, a further step may be carried out prior to transmitting the shear wave excitation pulse 11. In this step one reference pulse or a sequence of reference pulses which may be also transmitted along lines being laterally staggered one from the other and from the excitation point 1 are transmitted into the target body.

Combining the attenuation imaging steps with the elasticity imaging can be carried out in different ways.

One or more of the reference pulses and/or one or more of the tracking pulses transmitted into the ROI for carrying out elasticity imaging scans can be used also for computing the attenuation coefficients along each of the scanlines corresponding to one or more of the said reference or tracking pulses.

In one embodiment the reflected echoes of the transmitted ultrasound pulses of one or more of the reference pulses or of one or more of the tracking pulses can be used for carrying out the attenuation coefficient calculation and the elasticity evaluation along the corresponding scanline and at the corresponding depth.

In an alternative embodiment at least some or all the transmitted reference pulses and/o the transmitted tracking pulses can be repeated, and the corresponding echoes are used respectively for the attenuation coefficient calculation and for the elasticity estimation.

Figure 2:
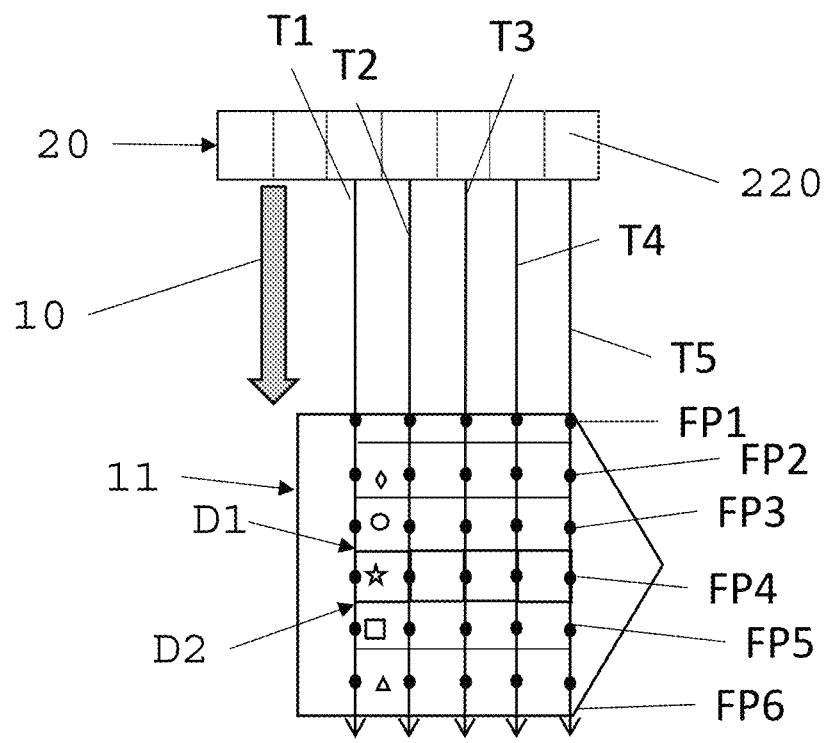
FIG. 2 is a schematic view of an ultrasound probe used for carrying out elasticity parameter measurements by means of shear waves.

FIG. 2 adds more details to the representation of FIG. 1 and is related to the case of combining attenuation imaging and elasticity imaging of the tissue in the ROI 2.

Figure 4:
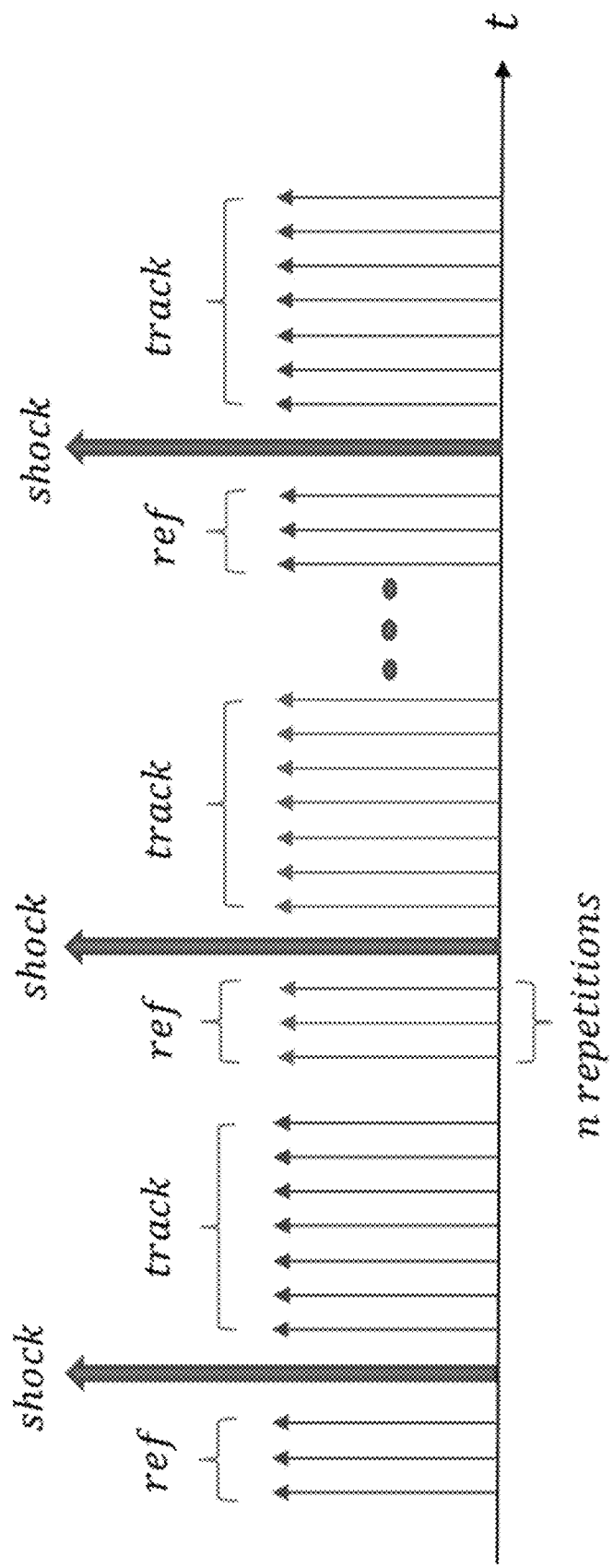
FIG. 4 is a schematic representation of a sequence of reference pulses, shock waves and tracking pulses for carrying out elasticity measurements and also attenuation parameter measurements.

For simplicity sake the reference pulses are not shown in this example, but it is clear for the skilled person how to integrate the present FIG. 2 in order to show also the reference pulses, particularly when considering FIG. 4 representing a sequence of transmission pulses comprising reference and tracking pulses and, in between the said reference and tracking pulses, the shear wave generation shock pulse is transmitted.

Here the probe 20 is represented diagrammatically as a linear array of transducers 220. The arrow 10 represents the tracking pulse focused at an excitation point or region along a certain line adjacent to the region of interest. The shear wave 11 is represented by the arrow and has a certain width in the depth direction i.e. in the direction of propagation of the tracking beams T1, T2, T3, T4 and T5 and the direction of propagation of the shear wave is indicated by the arrow like shape. The tracking beams T1 to T5 are focused each one along a line of sight of a plurality of lines of sight which are distributed over the extension of the region of interest. The term lateral means here in the direction of propagation of the shear wave 11.

Along each tracking line the corresponding tracking beam is focused at a certain number of tracking focal points FP1 to FP6 which are positioned at different depth in the region of interest.

Ultrasound tracking beams are repeatedly transmitted focused along the tracking lines and the received data are processed for determining the displacements of the tissue in the region of interest caused by the propagation of the shear wave.

The displacement is a mean displacement since it is averaged in the space, by grouping the displacement measurement between near pixels. On each tracking line, and at each tracking point along the corresponding tracking line the measurement of the displacement is repeated over time to form a sample curve representing the passage of the shear wave.

According to an embodiment such curve may be filtered by a moving mean such to eliminate noise.

For each tracking line and at each tracking focal point at the different depth the measured curve shows the displacement at the corresponding focal point as a function of time.

According to the present embodiment, the peak of the measured displacement is defined to find the shear wave propagation speed: the peak instant on each line of sight and at each tracking focal point FP1 to FP6 related to the known distance of the lines of sight from each other allows the propagation speed to be calculated.

Identifying the peak is the most simple and advantageous operation, but as an alternative it is possible to consider other significant points of the curve such as for example the maximum slope point or the correlation between the curves or the difference between curves.

According to the above process, the displacements inside the region of interest along each of the tracking lines and at the different depth of the tracking focal points are considered, such to reconstruct the shear wave propagation pattern by the measurement of all the tracking lines and the shear wave speed obtained from the said propagation pattern may be processed for calculating the distribution of the elasticity parameter along the region of interest.

According to an embodiment the examination may be structured in repeated acquisition sequences, and each sequence comprises the transmission of an acoustic excitation pulse at the excitation point and a measurement of the displacements at the tracking focal points of a single tracking line or of a plurality of tracking lines acquired in parallel.

When the measurement of the displacements induced by the propagation of the shear wave occurs line by line it is necessary to transmit an excitation pulse for each of the measurements on the different lines of sight acquired individually or in parallel.

For example, it is possible to acquire one line of sight a time or two or four lines of sight a time in parallel, with standard B-mode imaging techniques.

Tracking of the displacement data along two or more of the tracking lines can also be carried out in an interleaved manner for the two or more tracking lines relatively to each shear wave generation event after a shear wave excitation pulse of a sequence of excitation pulses.

According to an embodiment such sequence of excitation pulses has a limited number of excitation pulses transmitted with a certain repetition frequency and each series of excitation pulses is interrupted for a certain period by a cooling period before being carried out again. The B-mode image acquisition and the corresponding image may be frozen for the time during which a series of excitation pulses is being transmitted and the B-mode image may be refreshed by a new image acquisition during the cooling period between the repetition sequences of excitation pulses.

Such feature has also the advantage of allowing hardware to be prepared to perform a new transmission series of excitation pulses, and at the same time of allowing the probe and the tissues to cool.

In a further embodiment for each tracking line, before the transmission of the shear wave excitation pulse, one or more reference measurements on the line of sight under examination are carried out. Thus, the displacement at each of the tracking points can be measured in relation to a reference condition where the tissue in the region of interest is not disturbed by the passage of the shear wave.

According to a further embodiment, the data detected by the measurement of the shear wave are processed for filtering possible artefacts. Preferably such processing is carried out before the calculation of the displacement on each line of sight and the following calculation of the shear wave propagation speed.

In one embodiment, an ECG signal is recorded and the generation of ultrasound beams and the measurement of the displacement of pixels in the image induced by the shear wave passing through the region of interest are synchronized with the ECG signal.

Thus, the method can perform a triggering on the heartbeat, in order to try to suppress as much as possible the movement-related artefacts, for which the shear wave imaging is very sensitive.

This embodiment can be used for the measurement of the elasticity of any biological tissue involved by the cardiac movement, and it is particularly advantageous in relation to the measurement on the left part of the liver, that is the liver part affected by the heartbeat.

The processing of the acquired data for determining the elasticity data substantially is divided in the following macro-steps:

I. Processing all the repetitions of the acquisition of a line of sight to obtain the extraction of the pattern over time of the displacements of the tissue on such line of sight at each tracking focal point within the region of interest 2;

II. Processing the whole set of results deriving from the previous steps in order to obtain the shear wave speed distribution in the region of interest and out of these data the one or more elasticity parameters in different sub regions of the region of interest.

III. Generating a graphic representation of the calculated values of the elasticity parameter distribution in the region of interest in the form of an elasticity image by applying to the image pixels representing the corresponding sub region of the region of interest appearance features as a function of the said elasticity parameters.

IV. combining this elasticity image to the anatomical image of the region of interest, i.e. the B-mode image of the region of interest by maintaining the same scaling and the same topological relation of the sub regions in the elasticity image with the anatomical structure in the region of interest.

As already disclosed above with a more generic case, the RF reception signals corresponding to the reflected echoes of the transmitted pulses can be used also for calculating the attenuation coefficients of the tissue at the different depths ranges which are indicated by the geometric symbols.

The envelope of the reception signals obtained by the reflected echoes on one or more of the said tracking lines is subjected to processing for calculating the attenuation coefficient according to the steps already disclosed above and according to one of the two alternative embodiments.

The embodiment described in FIGS. 1 and 2 can be used for the measurement of the attenuation map of any biological tissue and it is particularly advantageous in relation to the measurement on the liver.

The processing of the acquired data for determining the attenuation data substantially is divided in the following macro-steps:

I. Processing all the repetitions of the acquisition of a line of sight to obtain the extraction of the pattern over time of the attenuation coefficients of the tissue on such line of sight at each tracking focal point within the region of interest 2;

II. Processing the whole set of results deriving from the previous steps in order to obtain the attenuation coefficient distribution in the region of interest and out of these data the one or more attenuation parameters in different sub regions of the region of interest.

III. Generating a graphic representation of the calculated values of the attenuation parameter distribution in the region of interest in the form of an attenuation coefficient or parameter image by applying to the image pixels representing the corresponding sub region of the region of interest appearance features as a function of the said attenuation parameters.

IV. Combining this attenuation image to the anatomical image of the region of interest, i.e. the B-mode image of the region of interest by maintaining the same scaling and the same topological relation of the sub regions in the attenuation image and/or in the elasticity image with the anatomical structure in the region of interest.

In a further embodiment the elasticity image can be also displayed in an overlapped manner or side by side, or it can be displayed alternatively to the attenuation image by simple commands.

According to a further variant embodiment the combined B-mode and elasticity data and the combined B-mode and attenuation data are displayed with two different images placed one beside the other on a display. One image showing elasticity data overlapped to the B-mode data and the other image showing attenuation data overlapped to the B-mode data.

On the graph of FIG. 2, the abscissa shows the propagation time and the ordinate the space, that is the position of the lines of sight. For each line of sight the maximum of the mean displacement along the line of sight, that corresponds to the wave peak, is identified and drawn in the graph.

FIG. 4 show a sequence of reference shock and tracking pulses which is typically applied for elasticity imaging and which can be used also for obtaining the data for calculating the attenuation image of a ROI.

Figure 5:
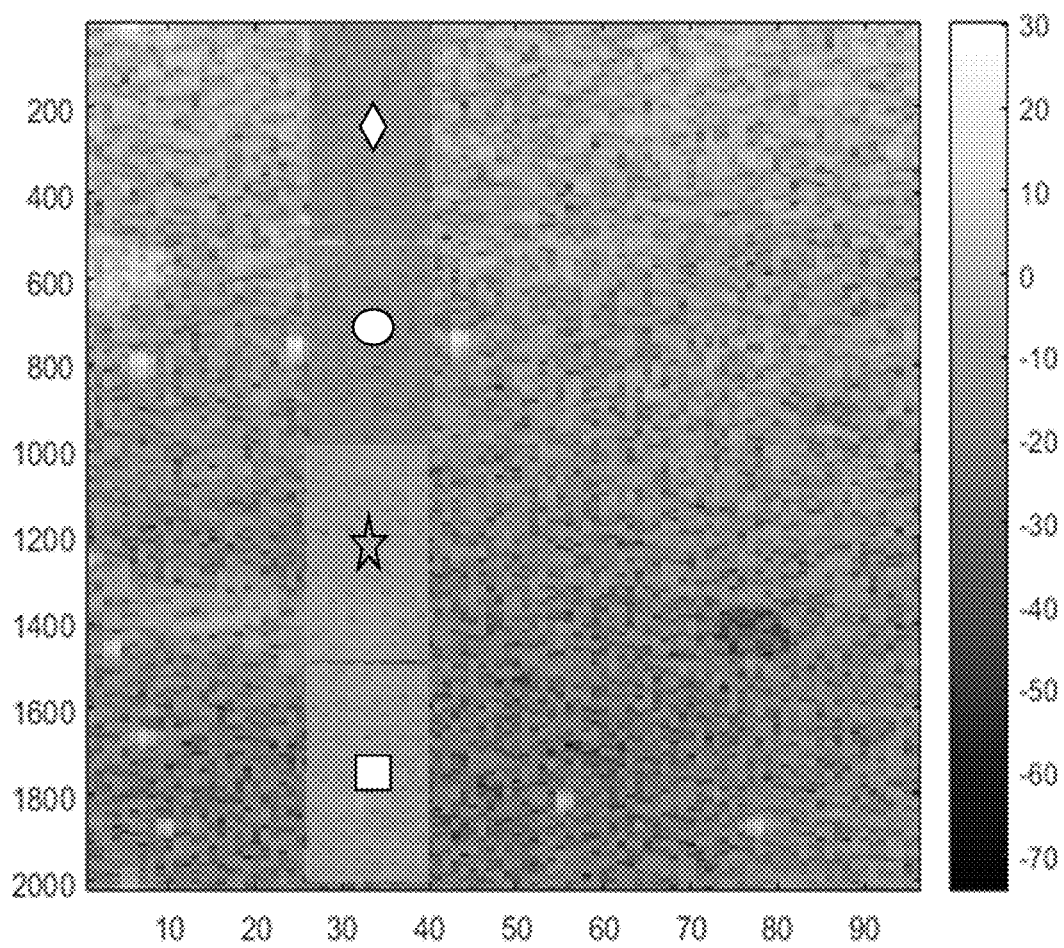
FIG. 5 shows an embodiment of a attenuation parameter map overlapped to a Bmode image of the same Region of Interest (ROI).

FIG. 5 shows an example of an attenuation map along a scan line which is overlapped on a B-mode image of the same ROI of the attenuation map.

The geometric symbols correspond to the ones in FIG. 2 and maintain a relation with the depth ranges of FIG. 2 showing where on the image map the said depth ranges are located.

Figure 6:
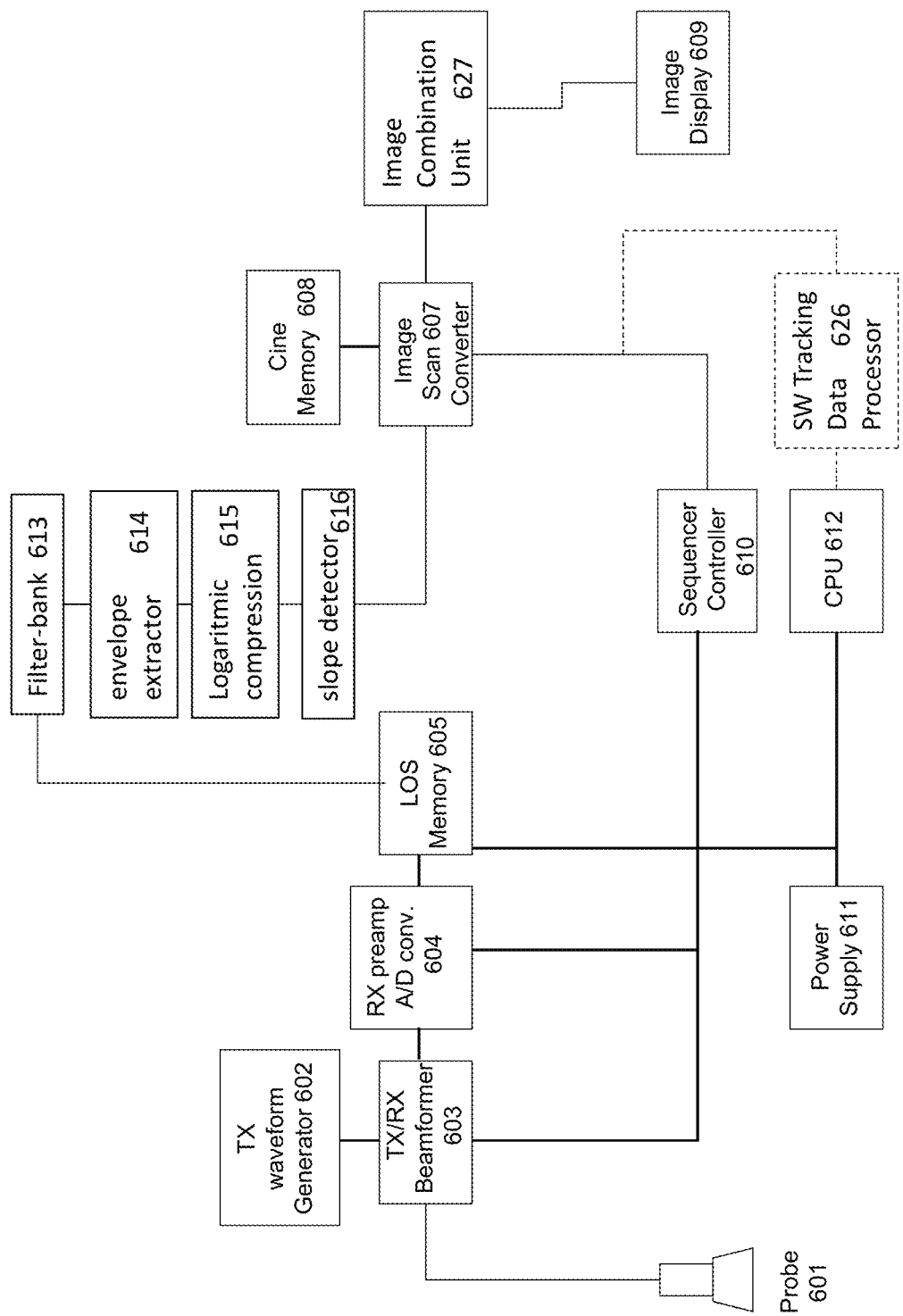
FIG. 6 illustrates a block diagram of the system according to an embodiment.

FIG. 6 illustrates a high-level block diagram of an ultrasound system. Portions of the system (as defined by various functional blocks) may be implemented with dedicated hardware, such as transmit/receive (TX/RX) driving/preamp and power switching circuitry, which may utilize analog components. Digital components, DSPs and/or FPGAs, may be utilized to implement the sequencer controller and the timing generator.

The ultrasound system of FIG. 6 includes one or more ultrasound probes 601, 620. The probe 601 may include various transducer array configurations, such as a one-dimensional array, a two-dimensional array, a linear array, a convex array and the like. The transducers of the array may be managed to operate as a 1D array, 1.25D array, 1.5D array, 1.75D array, 2D array, 3D array, 4D array, etc.

The ultrasound probe 601 is coupled over a wired or wireless link to a beamformer 603. The beamformer 603 includes a transmit (TX) beamformer and a receive (RX) beamformer that are jointly represented by TX/RX beamformer 603. The beamformer 603 supplies transmit signals to the probe 601 and performs beamforming of "echo" signals that are received by the probe 601.

A TX waveform generator 602 is coupled to the beamformer 603 and generates the transmit signals that are supplied from the beamformer 603 to the probe 601. The transmit signals may represent various types of ultrasound TX signals such as used in connection with B-mode imaging, colour Doppler imaging, pulse-inversion transmit techniques, contrast-based imaging, M-mode imaging and the like. In accordance with embodiments herein, the transmit signals include acoustic disturbance ultrasound (ACU) beam that are directed at select excitation points or regions (1 in FIG. 1A). The ACU beams are configured to generate shear waves as described herein.

The beamformer 603 performs beamforming upon received echo signals to form beamformed echo signals in connection pixel locations distributed across the region of interest. For example, in accordance with certain embodiments, the transducer elements generate raw analog receive signals that are supplied to the beamformer. The beamformer adjusts the delays to focus the receive signal along a select receive beam and at a select depth within the ROI. The beamformer adjusts the weighting of the receive signals to obtain a desired apodization and profile. The beamformer sums the delayed, weighted receive signals to form RF beamformed signals. The RF beamformed signals are digitized at a select sampling rate by the RX preamp and A/D converter 604. The RF beamformed signals are converted to I,Q data pairs.

The TX waveform generator 602, TX/RX beamformer 603 and A/D converter 604 cooperate to generate the acoustic disturbance ultrasound beams 10 directed at the excitation point 1. The acoustic disturbance ultrasound beams are configured to produce shear waves 11 that have directions of propagation extending laterally from the directions of propagation of the acoustic disturbance ultrasound beams 10. The I,Q data pairs are saved as image pixels in the line of sight (LOS) memory. For example, the LOS memory may include LOS memory portions associated with each line of sight through the ROI. The I,Q data pairs, defining the image pixels for corresponding individual ROI locations along a corresponding LOS, are saved in the corresponding LOS memory portion. A collection of image pixels (e.g., I,Q data pairs) are collected over time and saved in the LOS memory 605. The image pixels correspond to tissue and other anatomy within the ROI. As the ROI experiences the shear waves, the tissue and other anatomy in the ROI moves in response to the shear waves. The collection of image pixels captures the movement of tissue other anatomy within the ROI.

In embodiments, a dedicated sequencer/timing controller 610 may be programmed to manage acquisition timing which can be generalized as a sequence of firings aimed to locally generate shear waves aside the measurement box followed by tracking firings to monitor transition of the shear waves through the acquisition lines (LOS) in the measurement box (corresponding to the ROI). Optionally, idle phases can be added to control heating of the probe and manage compliance with safety emission regulations. According to a further option also reference pulses can be generated and transmitted along corresponding reference lines.

A sequence controller 610 manages operation of the TX/RX beamformer 603 and the A/D converter 604 in connection with transmitting ADU beams and measuring image pixels at individual LOS locations along the lines of sight. The sequence controller 610 manages collection of reference measurements and shear-wave induced measurements. The sequence controller 610 provides a pause period between a last measurement along one tracking line coincident with one line of sight and a first measurement along a following tracking line coincident with a following line of sight.

One or more processors perform various processing operations as described herein. The CPU 612 may perform one or more of the operations described herein in connection with generation of shear waves, measurement of displacement, calculation of displacement speed, calculation of stiffness values and the like.

Among other things, the processor and/or CPU 612 analyze the image pixels to measure displacement of the image pixels or controls an optional dedicated shear wave tracking data processor 626. The processor and/or the CPU 612 and or the optional shear wave data processor measure the displacement at image pixels for the plurality of lines of sight placed in the region of interest. The lines of sight are located at different predetermined laterally staggered distances from the excitation point (1), (4).

The processor 606 and/or CPU 612 or optionally a dedicated shear wave tracking data processor 626 also calculates a stiffness value based on the speed of the shear wave according to one or more of the examples describe above.

As explained herein, the processor and/or CPU 612 or the dedicated processor 626 obtaining one or more reference measurements for a plurality of lines of sight in the region of interest, prior to generating the first and second shear waves. According to an embodiment, the processor and/or CPU 612 or the optional dedicated processor 626 measure the shear waves 11 include measuring mean displacement over time of the tissue along a plurality of line of sights and identifying a peak of the mean displacements.

For example, the measurements by the processor and/or CPU 612 or the optional dedicated processor 626 may include calculating a cross-correlation between the measurements associated with the shear waves and a reference measurement obtained independent of the shear waves. The processor and/or CPU 612 or the optional dedicated processor 626 measure displacement over time of the tissue along a plurality of line of sights and calculates speeds of the shear waves 11 based, in part, on distances of the corresponding lines of sight from the excitation point 1.

The processor and/or CPU 612 also performs conventional ultrasound operations. For example, the processor executes a B/W module to generate B-mode images. The processor and/or CPU 612 executes a Doppler module to generate Doppler images. The processor executes a Color flow module (CFM) to generate colour flow images. The processor and/or CPU 612 may implement additional ultrasound imaging and measurement operations. Optionally, the processor and/or CPU 612 may filter the displacements to eliminate movement-related artifacts.

An image scan converter 607 performs scan conversion on the image pixels to convert the format of the image pixels from the coordinate system of the ultrasound acquisition signal path (e.g., the beamformer, etc.) and the coordinate system of the display. For example, the scan converter 607 may convert the image pixels from polar coordinates to Cartesian coordinates for image frames.

A cine memory 608 stores a collection of image frames over time. The image frames may be stored formatted in polar coordinates, Cartesian coordinates or another coordinate system.

An image display 609 displays various ultrasound information, such as the image frames and information measured in accordance with embodiments herein. For example, the image display 609 displays the stiffness values, displacement measurements, displacement speeds, and other information calculated in accordance with embodiments herein. The stiffness values, displacement measurements, displacement speeds, and other information may be displayed as image information, as numeric values, graphical information and the like. The display 609 displays the ultrasound image with the region of interest shown. Optionally, the display 609 may display indicia indicating the excitation points (1), where the indicia are overlaid on the ultrasound image and/or presented along opposite sides of the ultrasound image.

Optionally, the system of FIG. 6 may include an ECG monitor not shown in detail that couples an ECG sensor to the patient and records an ECG signal indicative of the patient's heart rate. The processor and/or sequence controller 610 synchronize the generation of acoustic disturbance ultrasound beams 10 and the measurement of the first and second displacements of the image pixels induced by the first and second shear waves 11 with the ECG signal.

According to the present invention the embodiment of FIG. 6 shows an envelope extractor 614 which generates the envelope of the RF reception signals corresponding to the received echoes along one or more of the reference and tracking scan lines. The envelope generated in the extractor 614 is subjected to logarithmic compression in 615. A slope detector 616 computes the slope of lines fitting the logarithm of the envelope at different depths as already disclosed in relation to method in the present description and in the preceding paragraphs.

A map is generated in which an attenuation coefficient calculated for a certain depth range and along a certain scan line is represented by a color hue scale and in the position corresponding to the pixel or voxel at the said depth range and along the said scan line.

The blocks/modules illustrated in FIG. 6 can be implemented with dedicated hardware (DPSs, FPGAs, memories) and/or in software with one or more processors.

A control CPU module 612 is configured to perform various tasks such as implementing the user/interface and overall system configuration/control. In case of fully software implementation of the ultrasound signal path, the processing node usually hosts also the functions of the control CPU.

A power supply circuit 611 is provided to supply power to the various circuits, modules, processors, memory components, and the like. The power front-end may be an A.C. power source and/or a battery power source (e.g., in connection with portable operation).

Optionally, in point Shear Wave acquisition, the RX tracking lines (line of sights—LOSs) may be temporarily stored, either as pure RF or as I/Q data, in the front-end local memories. The processing may be implemented by a dedicated processor module and/or a CPU 612. Processed data may be formatted as shear wave speed measurements or stiffness values. These are then added to the ancillary data of the field-of-view under scan and properly reported as an overlay to the image displayed on system's monitor.

According to a further feature, an image combination unit 627 may be present in which the B-mode image data of at least of a region of interest and the corresponding graphic representation as an image of the velocity of the shear wave or of the elasticity parameter determined from said velocity data and/or the attenuation data is combined for the superimposed display of the B-mode image and of the image representing the shear wave velocity and/or the elasticity features determined for the corresponding pixels in the B-mode image. The representation as an image of the velocity or of the corresponding elasticity parameter values and the representation of the attenuation coefficients and the combination of this image with the B-mode image can be carried out according to one of the previously disclosed methods.

Figure 7:
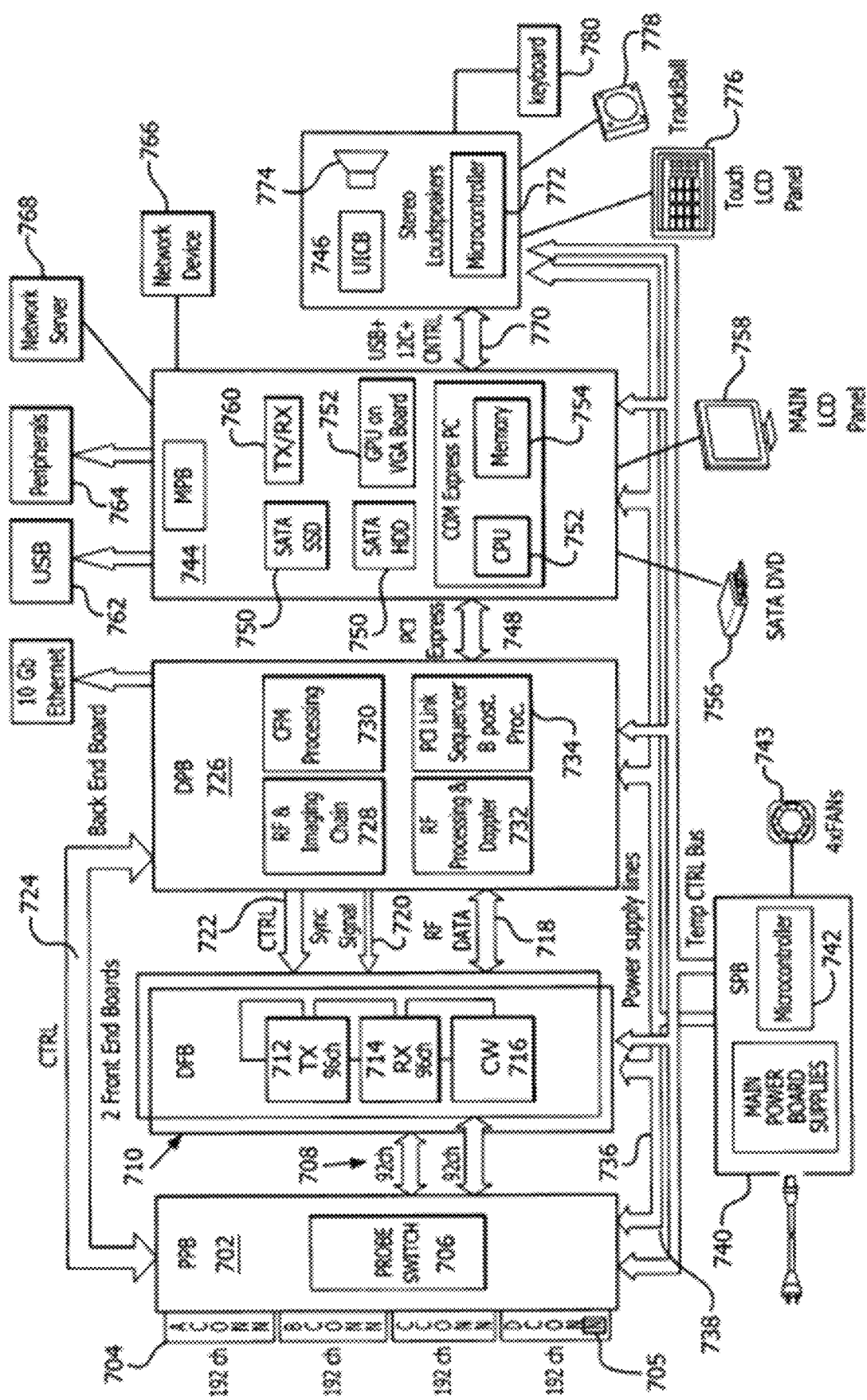
FIG. 7 illustrates a block diagram of an ultrasound system formed in accordance with an alternative embodiment.

FIG. 7 illustrates a block diagram of an ultrasound system formed in accordance with an alternative embodiment. The system of FIG. 7 implements the operations described herein in connection with various embodiments. By way of example, one or more circuits/processors within the system implement the operations of any processes illustrated in connection with the figures and/or described herein. The system includes a probe interconnect board 702 that includes one or more probe connection ports 704. The connection ports 704 may support various numbers of signal channels (e.g., 128, 192, 256, etc.). The connector ports 704 may be configured to be used with different types of probe arrays (e.g., phased array, linear array, curved array, 1D, 1.25D, 1.5D, 1.75D, 2D array, etc.). The probes may be configured for different types of applications, such as abdominal, cardiac, maternity, gynecological, urological and cerebrovascular examination, breast examination and the like.

One or more of the connection ports 704 may support acquisition of 2D image data and/or one or more of the connection ports 704 may support 3D image data. By way of example only, the 3D image data may be acquired through physical movement (e.g., mechanically sweeping or physician movement) of the probe and/or by a probe that electrically or mechanically steers the transducer array.

The probe interconnect board (PIB) 702 includes a switching circuit 706 to select between the connection ports 704. The switching circuit 706 may be manually managed based on user inputs. For example, a user may designate a connection port 704 by selecting a button, switch or other input on the system. Optionally, the user may select a connection port 704 by entering a selection through a user interface on the system.

Optionally, the switching circuit 706 may automatically switch to one of the connection ports 704 in response to detecting a presence of a mating connection of a probe. For example, the switching circuit 706 may receive a "connect" signal indicating that a probe has been connected to a selected one of the connection ports 704. The connect signal may be generated by the probe when power is initially supplied to the probe when coupled to the connection port 704. Additionally, or alternatively, each connection port 704 may include a sensor 705 that detects when a mating connection on a cable of a probe has been interconnected with the corresponding connection port 704. The sensor 705 provides signal to the switching circuit 706, and in response thereto, the switching circuit 706 couples the corresponding connection port 704 to PIB outputs 708. Optionally, the sensor 705 may be constructed as a circuit with contacts provided at the connection ports 704. The circuit remains open when no mating connected is joined to the corresponding connection port 704. The circuit is closed when the mating connector of a probe is joined to the connection port 704.

A control line 724 conveys control signals between the probe interconnection board 702 and a digital processing board 724. A power supply line 736 provides power from a power supply 740 to the various components of the system, including but not limited to, the probe interconnection board (PIB) 702, digital front-end boards (DFB) 710, digital processing board (DPB) 726, the master processing board (M PB) 744, and a user interface control board (UI CB) 746. A temporary control bus 738 interconnects, and provides temporary control signals between, the power supply 740 and the boards 702, 710, 726, 744 and 746. The power supply 740 includes a cable to be coupled to an external AC power supply. Optionally, the power supply 740 may include one or more power storage devices (e.g. batteries) that provide power when the AC power supply is interrupted or disconnected. The power supply 740 includes a controller 742 that manages operation of the power supply 740 including operation of the storage devices.

Additionally, or alternatively, the power supply 740 may include alternative power sources, such as solar panels and the like. One or more fans 743 are coupled to the power supply 740 and are managed by the controller 742 to be turned on and off based on operating parameters (e.g. temperature) of the various circuit boards and electronic components within the overall system (e.g. to prevent overheating of the various electronics).

The digital front-end boards 710 providing analog interface to and from probes connected to the probe interconnection board 702. The DFB 710 also provides pulse or control and drive signals, manages analog gains, includes analog to digital converters in connection with each receive channel, provides transmit beamforming management and receive beamforming management and vector composition (associated with focusing during receive operations).

The digital front-end boards 710 include transmit driver circuits 712 that generate transmit signals that are passed over corresponding channels to the corresponding transducers in connection with ultrasound transmit firing operations. The transmit driver circuits 712 provide pulse or control for each drive signal and transmit beamforming management to steer firing operations to points of interest within the region of interest. By way of example, a separate transmit driver circuits 712 may be provided in connection with each individual channel, or a common transmit driver circuits 712 may be utilized to drive multiple channels. The transmit driver circuits 712 cooperate to focus transmit beams to one or more select points within the region of interest. The transmit driver circuits 712 may implement single line transmit, encoded firing sequences, multiline transmitter operations, generation of shear wave inducing ultrasound beams as well as other forms of ultrasound transmission techniques.

The digital front-end boards 710 include receive beamformer circuits 714 that received echo/receive signals and perform various analog and digital processing thereon, as well as phase shifting, time delaying and other operations in connection with beamforming. The beam former circuits 714 may implement various types of beamforming, such as single-line acquisition, multiline acquisition as well as other ultrasound beamforming techniques.

The digital front-end boards 716 include continuous wave Doppler processing circuits 716 configured to perform continuous wave Doppler processing upon received echo signals. Optionally, the continuous wave Doppler circuits 716 may also generate continuous wave Doppler transmit signals.

The digital front-end boards 710 are coupled to the digital processing board 726 through various buses and control lines, such as control lines 722, synchronization lines 720 and one or more data bus 718. The control lines 722 and synchronization lines 720 provide control information and data, as well as synchronization signals, to the transmit drive circuits 712, receive beamforming circuits 714 and continuous wave Doppler circuits 716. The data bus 718 conveys RF ultrasound data from the digital front-end boards 710 to the digital processing board 726. Optionally, the digital front-end boards 710 may convert the RF ultrasound data to I,Q data pairs which are then passed to the digital processing board 726.

The digital processing board 726 includes an RF and imaging module 728, a colour flow processing module 730, an RF processing and Doppler module 732 and a PCI link module 734. The digital processing board 726 performs RF filtering and processing, processing of black and white image information, processing in connection with colour flow, Doppler mode processing (e.g. in connection with polls wise and continuous wave Doppler). The digital processing board 726 also provides image filtering (e.g. speckle reduction) and scanner timing control. The digital processing board 726 may include other modules based upon the ultrasound image processing functionality afforded by the system.

The modules 728-734 comprise one or more processors, DSPs, and/or FPGAs, and memory storing program instructions to direct the processors, DSPs, and/or FPGAs to perform various ultrasound image processing operations. The RF and imaging module 728 perform various ultrasound related imaging, such as B mode related image processing of the RF data. The RF processing and Doppler module 732 convert incoming RF data to I,Q data pairs, and performs Doppler related processing on the I, Q data pairs. Optionally, the imaging module 728 may perform B mode related image processing upon I, Q data pairs. The CFM processing module 730 performs colour flow related image processing upon the ultrasound RF data and/or the I, Q data pairs. The PCI link 734 manages transfer of ultrasound data, control data and other information, over a PCI express bus 748, between the digital processing board 726 and the master processing board 744.

The master processing board 744 includes memory 750 (e.g. serial ATA solid-state devices, serial ATA hard disk drives, etc.), a VGA board 752 that includes one or more graphic processing unit (GPUs), one or more transceivers 760 one or more CPUs 752 and memory 754. The master processing board (also referred to as a PC board) provides user interface management, scan conversion and cine loop management. The master processing board 744 may be connected to one or more external devices, such as a DVD player 756, and one or more displays 758. The master processing board includes communications interfaces, such as one or more USB ports 762 and one or more ports 764 configured to be coupled to peripheral devices. The master processing board 744 is configured to maintain communication with various types of network devices 766 and various network servers 768, such as over wireless links through the transceiver 760 and/or through a network connection (e.g. via USB connector 762 and/or peripheral connector 764).

The network devices 766 may represent portable or desktop devices, such as smart phones, personal digital assistants, tablet devices, laptop computers, desktop computers, smart watches, ECG monitors, patient monitors, and the like. The master processing board 744 conveys ultrasound images, ultrasound data, patient data and other information and content to the network devices for presentation to the user. The master processing board 744 receives, from the network devices 766, inputs, requests, data entry and the like.

The network server 768 may represent part of a medical network, such as a hospital, a healthcare network, a third-party healthcare service provider, a medical equipment maintenance service, a medical equipment manufacturer, a government healthcare service and the like. The communications link to the network server 768 may be over the Internet, a private intranet, a local area network, a wide-area network, and the like.

The master processing board 744 is connected, via a communications link 770 with a user interface control board 746. The communications link 770 conveys data and information between the user interface and the master processing board 744. The user interface control board 746 includes one or more processors 772, one or more audio/video components 774 (e.g. speakers, a display, etc.). The user interface control board 746 is coupled to one or more user interface input/output devices, such as an LCD touch panel 776, a trackball 778, a keyboard 780 and the like. The processor 772 manages operation of the LCD touch panel 776, as well as collecting user inputs via the touch panel 776, trackball 778 and keyboard 780, where such user inputs are conveyed to the master processing board 744 in connection with implementing embodiments herein.

Figure 8:
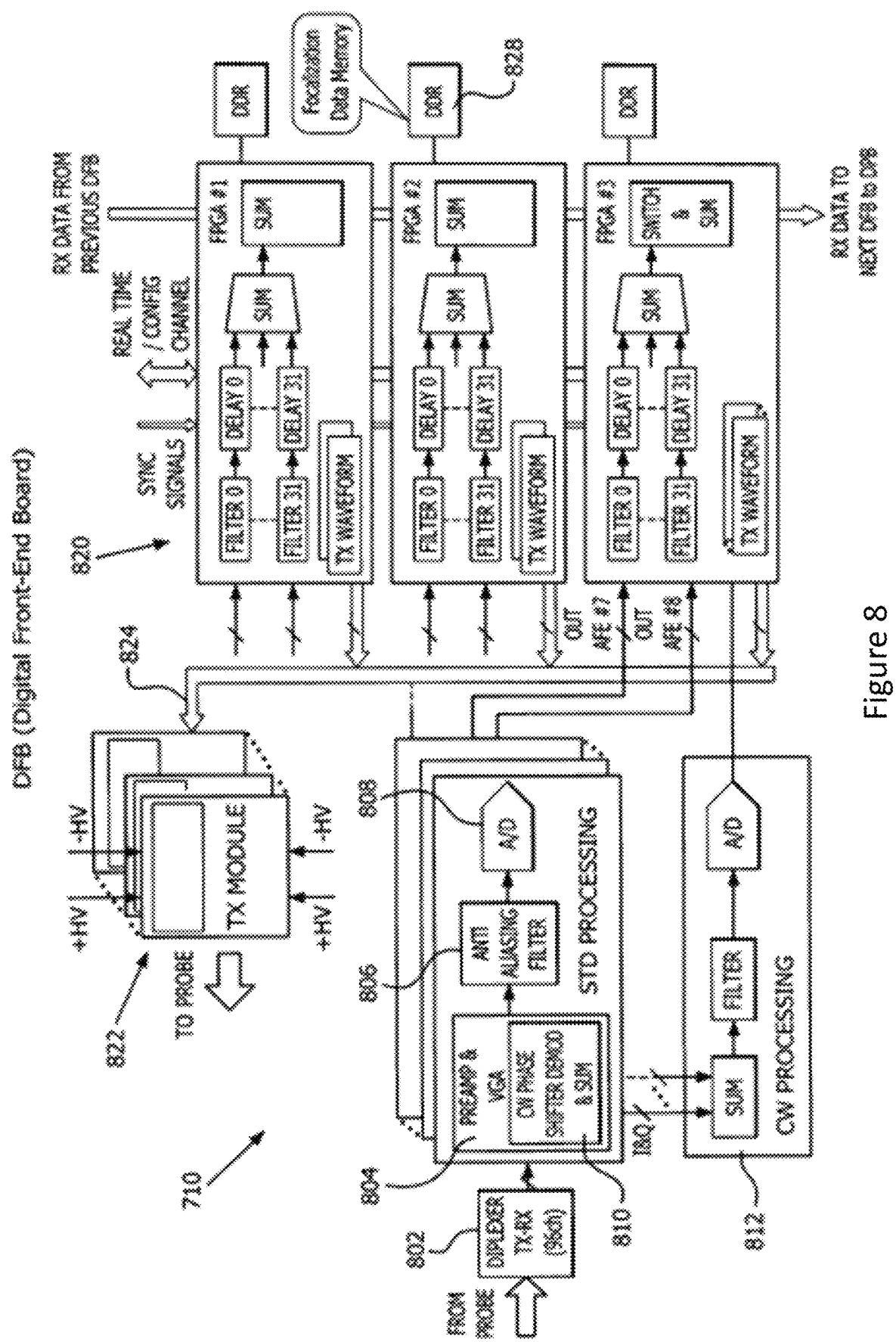
FIG. 8 illustrates a block diagram of a portion of the digital front-end boards.

FIG. 8 illustrates a block diagram of a portion of the digital front-end boards 710 formed in accordance with embodiments herein. A group of diplexers 802 receive the ultrasound signals for the individual channels over the PIB output 808. The ultrasound signals are passed along a standard processing circuit 805 or to a continuous wave processing circuit 812, based upon the type of probing utilized. When processed by the standard processing circuit 805, a preamplifier and variable gain amplifier 804 process the incoming ultrasound receive signals that are then provided to an anti-aliasing filter 806 which performs anti-aliasing filtering.

According to an embodiment the retrospective transmit beam focusing according to the present invention may be applied to the RF data directly acquired by the system or to transformed data according to different transformations as for example as a phase/quadrature (I/Q) transformation, or similar.

In the embodiment of FIG. 8 an example of the said transformation of the RF data is disclosed According to this example, the output of the filter 806 is provided to an A/D converter 808 that digitizes the incoming analog ultrasound receive signals. When a continuous wave (CW) probe is utilized, the signals therefrom are provided to a continuous wave phase shifter, demodulator and summer 810 which converts the analog RF reception signals to I,Q data pairs. The CW I,Q data pairs are summed, filtered and digitized by a continuous wave processing circuit 812. Outputs from the standard or continuous wave processing circuits 805, 812 are then passed to beam forming circuits 820 which utilize one or more FPGAs to perform filtering, delaying and summing the incoming digitized receive signals before passing the RF data to the digital processing board 826 (FIG. 7). The FPGAs receive focalization data from memories 828. The focalization data is utilized to manage the filters, delays and summing operations performed by the FPGAs in connection with beamforming. The beamformed RF or I/Q data is passed between the beamforming circuits 820 and ultimately to the digital processing board 726.

The digital front-end boards 710 also include transmit modules 822 that provide transmit drive signals to corresponding transducers of the ultrasound probe. The beamforming circuits 820 include memory that stores transmit waveforms. The transmit modules 822 receive transmit waveforms over line 824 from the beamforming circuits 820.

Figure 9:
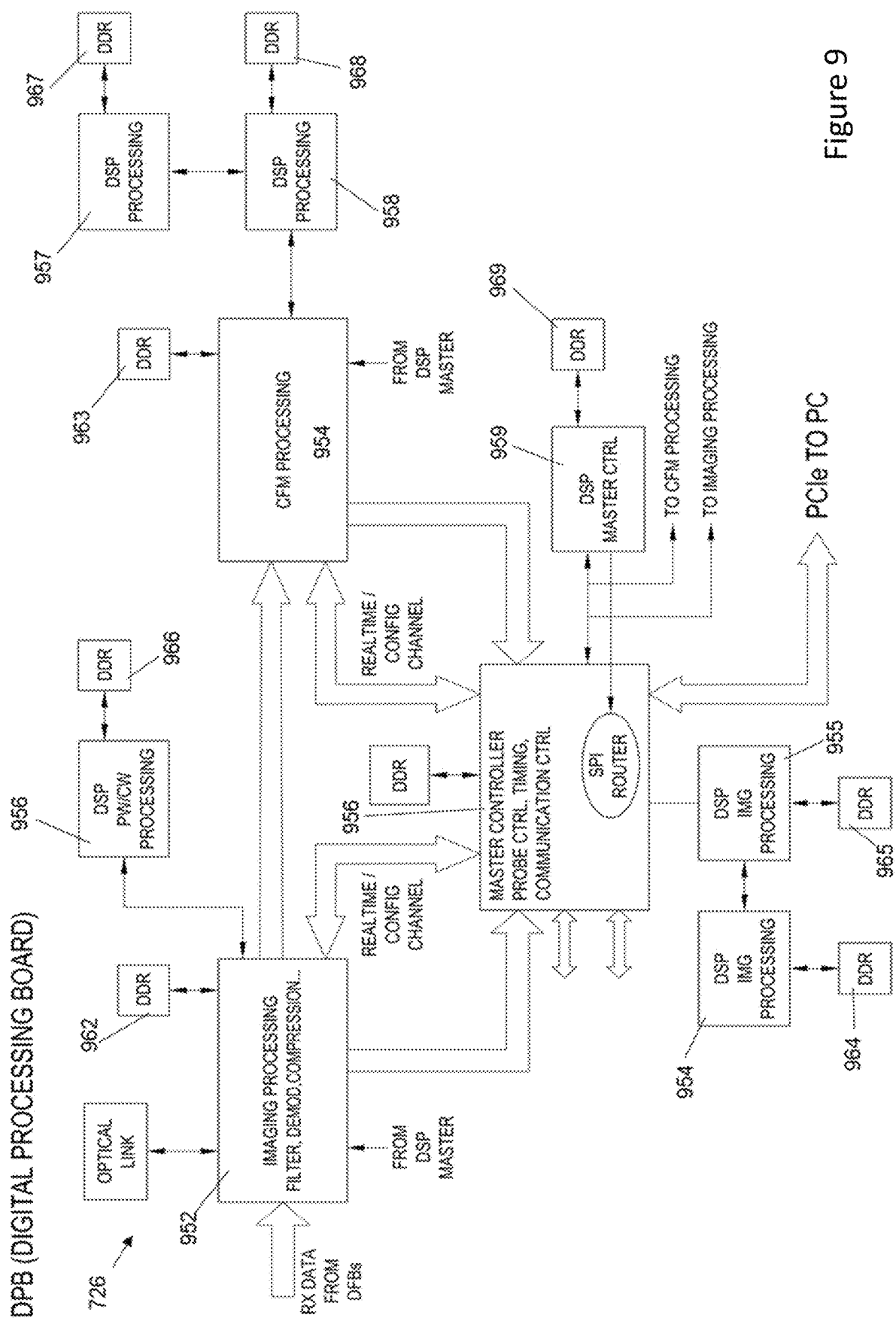
FIG. 9 illustrates a block diagram of the digital processing board.

FIG. 9 illustrates a block diagram of the digital processing board 726 implemented in accordance with embodiments herein. The digital processing board 726 includes various processors 952-959 to perform different operations under the control of program instructions saved within corresponding memories see 962-969. A master controller 950 manages operation of the digital processing board 726 and the processors 952-959. By way of example, one or more processors as the 952 may perform filtering, the modulation, compression and other operations, while another processor 953 performs colour flow processing. The master controller provides probe control signals, timing control signals, communications control and the like. The master controller 950 provides real-time configuration information and synchronization signals in connection with each channel to the digital front-end board 710.

Figure 10:
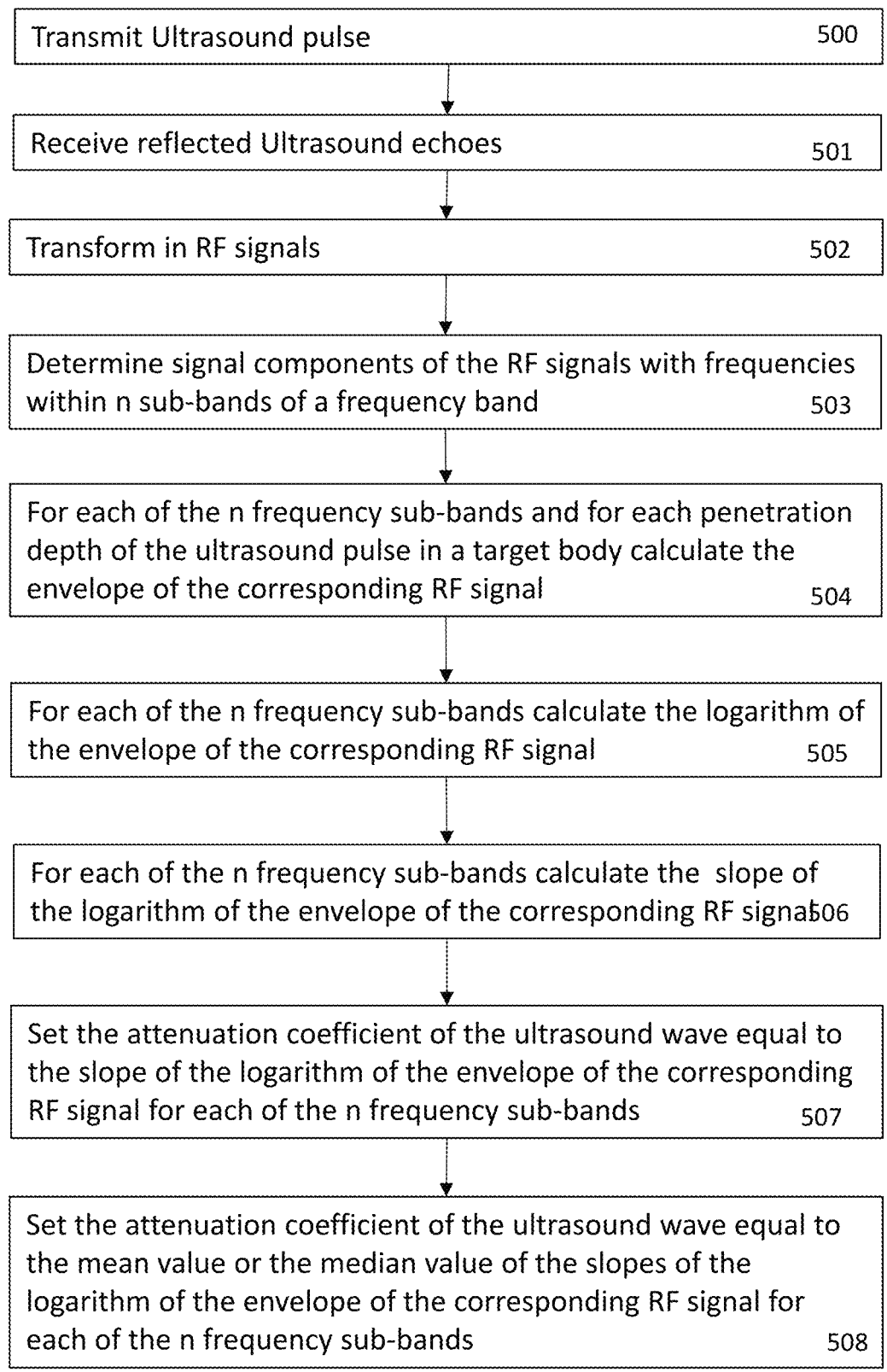
FIG. 10 and FIG. 11 show a work flow diagram of embodiments of the present invention.

FIG. 10 is a flowchart of an embodiment of the present method. Particularly example of FIG. 10 relates to the case in which a transmitted pulse of multifrequency band is generated and transmitted into the ROI.

Step 500 provides for the transmission of at least one ultrasound pulse in a ROI of a target body. The received echoes of the said pulse at step 501 are transformed by the probe in RF reception signals at step 502. The RF reception signals are subjected to filtering with a filter-bank for determining signal components of the RF signals with frequencies within n sub-bands of a frequency band as illustrated at step 503.

Step 504 provides for calculating the envelope of the corresponding RF signal for each of the n frequency sub-bands and for each penetration depth of the ultrasound pulse in a target body.

In step 505 for each of the n frequency subbands the logarithm of the envelope of the corresponding RF signal is calculated and in step 506 the slope of the logarithm of the envelope of the corresponding RF signal is calculated for each of the n frequency subbands.

Step 507 provides for setting the attenuation coefficient of the ultrasound wave equal to the slope of the logarithm of the envelope of the corresponding RF signal for each of the n frequency subbands.

In step 508 the attenuation coefficient of the ultrasound wave is set equal to the mean value or the median value of the slopes of the logarithm of the envelope of the corresponding RF signal for each of the n frequency subbands.

Figure 11:
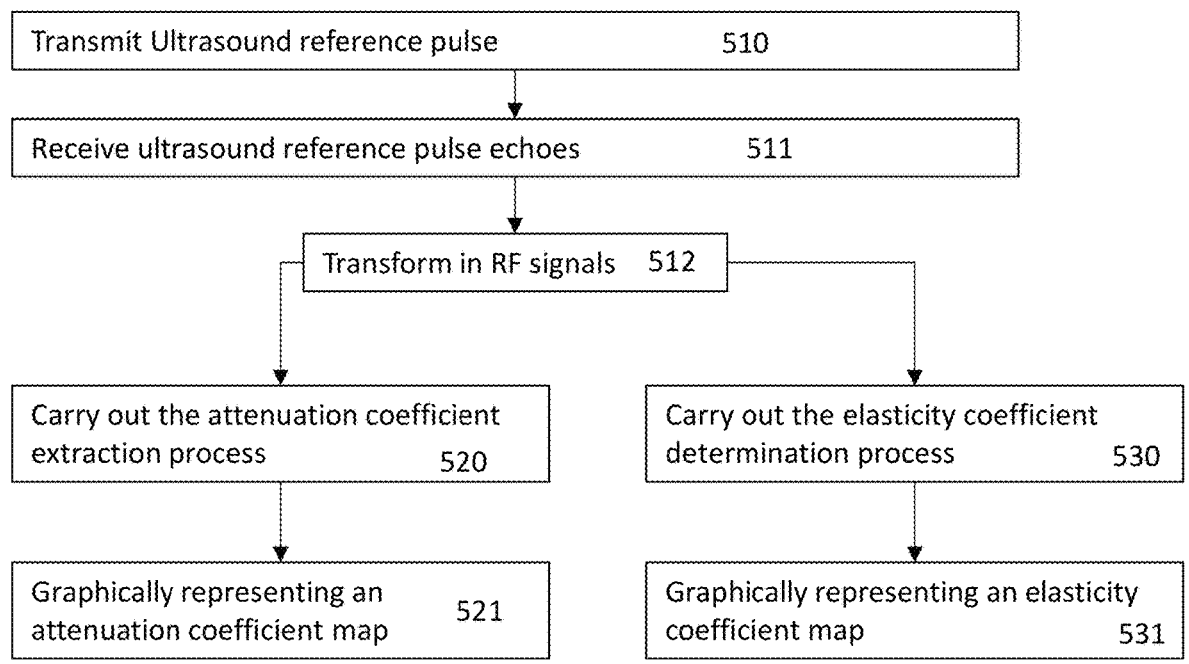

FIG. 11 show a flowchart relating to the embodiment of the present invention according to which the attenuation imaging is combined with the elasticity imaging within one image acquisition process.

AT step 510 one or a sequence of ultrasound reference pulses is transmitted into a target body. The echoes of the said transmit signals is received at step 511 and transformed in RF reception signals at step 512.

According to the one embodiment of the present invention the RF reception signals are used for carrying out the attenuation coefficient extraction process and graphically representing an attenuation coefficient map as indicated by steps 520 and 521 and also for carrying out the elasticity coefficient determination process and graphically representing an elasticity coefficient map as indicated by the steps 530 and 531.

Further embodiments which are already disclosed can be easily derived from the present flow chart. In the case the tracking pulses are used instead of the reference pulses or the said tracking pulses are used in combination with the said reference pulses and also in the case in which the said reference or tracking pulses are transmitted twice one time for carrying out the attenuation imaging modality and the other for carrying out the elasticity imaging modality.

It should be clearly understood that the various arrangements and processes broadly described and illustrated with respect to the figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

Aspects are described herein with reference to the figures, which illustrate example methods, devices and program products according to various example embodiments. These program instructions may be provided to a processor of a general-purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

One or more of the operations described above in connection with the methods may be performed using one or more processors. The different devices in the systems described herein may represent one or more processors, and two or more of these devices may include at least one of the same processors. In one embodiment, the operations described herein may represent actions performed when one or more processors (e.g., of the devices described herein) execute program instructions stored in memory (for example, software stored on a tangible and non-transitory computer readable storage medium, such as a computer hard drive, ROM, RAM, or the like).

The processor(s) may execute a set of instructions that are stored in one or more storage elements, in order to process data. The storage elements may also store data or other information as desired or needed. The storage element may be in the form of an information source or a physical memory element within the controllers and the controller device. The set of instructions may include various commands that instruct the controllers and the controller device to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

The controller may include any processor-based or microprocessor-based system including systems using microcontrollers, reduced instruction set computers (RISC), application specific integrated circuitry (ASICs), field-programmable gate arrays (FPGAs), logic circuitry, and any other circuit or processor capable of executing the functions described herein. When processor-based, the controller executes program instructions stored in memory to perform the corresponding operations. Additionally, or alternatively, the controllers and the controller device may represent circuitry that may be implemented as hardware. The above examples are exemplary only, and are thus not intended to limit in any way the definition and/or meaning of the term "controller."

Optionally, aspects of the processes described herein may be performed over one or more networks one a network server. The network may support communications using any of a variety of commercially-available protocols, such as Transmission Control Protocol/Internet Protocol ("TCP/IP"), User Datagram Protocol ("UDP"), protocols operating in various layers of the Open System Interconnection ("OSI") model, File Transfer Protocol ("FTP"), Universal Plug and Play ("UpnP"), Network File System ("NFS"), Common Internet File System ("CIFS") and AppleTalk. The network can be, for example, a local area network, a wide-area network, a virtual private network, the Internet, an intranet, an extranet, a public switched telephone network, an infrared network, a wireless network, a satellite network and any combination thereof.

In embodiments utilizing a web server, the web server can run any of a variety of server or mid-tier applications, including Hypertext Transfer Protocol ("HTTP") servers, FTP servers, Common Gateway Interface ("CGI") servers, data servers, Java servers, Apache servers and business application servers. The server(s) also may be capable of executing programs or scripts in response to requests from user devices, such as by executing one or more web applications that may be implemented as one or more scripts or programs written in any programming language, such as Java®, C, C# or C++, or any scripting language, such as Ruby, PHP, Perl, Python or TCL, as well as combinations thereof. The server(s) may also include database servers, including without limitation those commercially available from Oracle®, Microsoft®, Sybase® and IBM® as well as open-source servers such as MySQL, Postgres, SQLite, MongoDB, and any other server capable of storing, retrieving and accessing structured or unstructured data. Database servers may include table-based servers, document-based servers, unstructured servers, relational servers, non-relational servers or combinations of these and/or other database servers.

The embodiments described herein may include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers or other network devices may be stored locally and/or remotely, as appropriate. Where a system includes computerized devices, each such device can include hardware elements that may be electrically coupled via a bus, the elements including, for example, at least one central processing unit ("CPU" or "processor"), at least one input device (e.g., a mouse, keyboard, controller, touch screen or keypad) and at least one output device (e.g., a display device, printer or speaker). Such a system may also include one or more storage devices, such as disk drives, optical storage devices and solid-state storage devices such as random access memory ("RAM") or read-only memory ("ROM"), as well as removable media devices, memory cards, flash cards, etc.

Such devices also can include a computer-readable storage media reader, a communications device (e.g., a modem, a network card (wireless or wired), an infrared communication device, etc.) and working memory as described above. The computer-readable storage media reader can be connected with, or configured to receive, a computer-readable storage medium, representing remote, local, fixed and/or removable storage devices as well as storage media for temporarily and/or more permanently containing, storing, transmitting and retrieving computer-readable information. The system and various devices also typically will include a number of software applications, modules, services or other elements located within at least one working memory device, including an operating system and application programs, such as a client application or web browser. It should be appreciated that alternate embodiments may have numerous variations from that described above. For example, customized hardware might also be used and/or particular elements might be implemented in hardware, software (including portable software, such as applets) or both. Further, connection to other computing devices such as network input/output devices may be employed.

Various embodiments may further include receiving, sending, or storing instructions and/or data implemented in accordance with the foregoing description upon a computer-readable medium. Storage media and computer readable media for containing code, or portions of code, can include any appropriate media known or used in the art, including storage media and communication media, such as, but not limited to, volatile and non-volatile, removable and non-removable media implemented in any method or technology for storage and/or transmission of information such as computer readable instructions, data structures, program modules or other data, including RAM, ROM, Electrically Erasable Programmable Read-Only Memory ("EEPROM"), flash memory or other memory technology, Compact Disc Read-Only Memory ("CD-ROM"), digital versatile disk (DVD) or other optical storage, magnetic cassettes, magnetic tape, magnetic disk storage or other magnetic storage devices or any other medium which can be used to store the desired information and which can be accessed by the system device. Based on the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the invention as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions and equivalents falling within the spirit and scope of the invention, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including" and "containing" are to be construed as open-ended terms (i.e., meaning "including, but not limited to,") unless otherwise noted. The term "connected," when unmodified and referring to physical connections, is to be construed as partly or wholly contained within, attached to or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. The use of the term "set" (e.g., "a set of items") or "subset" unless otherwise noted or contradicted by context, is to be construed as a nonempty collection comprising one or more members. Further, unless otherwise noted or contradicted by context, the term "subset" of a corresponding set does not necessarily denote a proper subset of the corresponding set, but the subset and the corresponding set may be equal.

Operations of processes described herein can be performed in any suitable order unless otherwise indicated herein or otherwise clearly contradicted by context. Processes described herein (or variations and/or combinations thereof) may be performed under the control of one or more computer systems configured with executable instructions and may be implemented as code (e.g., executable instructions, one or more computer programs or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

Preferred embodiments of this disclosure are described herein, including the best mode known to the inventors for carrying out the invention. Variations of those preferred embodiments may become apparent to those of ordinary skill in the art upon reading the foregoing description. The inventors expect skilled artisans to employ such variations as appropriate and the inventors intend for embodiments of the present disclosure to be practiced otherwise than as specifically described herein. Accordingly, the scope of the present disclosure includes all modifications and equivalents of the subject matter recited in the claims appended hereto as permitted by applicable law. Moreover, any combination of the above-described elements in all possible variations thereof is encompassed by the scope of the present disclosure unless otherwise indicated herein or otherwise clearly contradicted by context.

All references, including publications, patent applications and patents, cited herein are hereby incorporated by reference to the same extent as if each reference were individually and specifically indicated to be incorporated by reference and were set forth in its entirety herein.

The invention claimed is:

1. Method for tissue characterization by ultrasound wave attenuation measurements wherein a shear wave velocity coefficient is estimated, comprising:
   a) acquiring an ultrasound image;

b) defining a region of interest in the image, the region of interest including image pixels;
c) transmitting at least an ultrasound pulse in a target body, the ultrasound pulse being an acoustic disturbance ultrasound beam directed at an excitation point, the acoustic disturbance ultrasound beam configured to produce a shear wave (11) that has a direction of propagation extending laterally from a direction of propagation of the acoustic disturbance ultrasound beam;
d) transmitting a sequence of ultrasound tracking pulses which are laterally staggered at different lateral positions relative to the excitation point and receiving corresponding reception signals;
e1) measuring displacements of the image pixels induced by the shear wave (11) by the ultrasound tracking pulses and assessing propagation speed of the shear wave in the direction of the lateral displacement of the tracking pulses and/or a stiffness value of tissue in the region of interest based on the displacements measured at step d);
e2) at least some of the reception signals generated by reflection of the one or more of the tracking pulses being transformed into RF reception signals for computing the propagation depth dependent attenuation coefficient at predetermined propagation depths by:
f) extracting an envelope of at least one of the RF reception signals;
g) carrying out a logarithmic compression of the extracted envelope; and
h) computing a propagation depth dependent attenuation coefficient of the tissues crossed by the ultrasound pulse in the target body as the slope of a line fitting logarithmic compressed envelope data along a penetration depth of the ultrasound pulse in the target body;
wherein at least one of the tracking pulses in the sequence of ultrasound tracking pulses is transmitted at least twice to correspond to at least two instances of a repeated tracking pulse, and received signals due to a reflected pulse of one of the of at least two instances of the repeated tracking pulse are used for computing the shear wave velocity while the received signals due to a reflected pulse of another of the at least two instances of the repeated tracking pulse are used for computing the propagation depth dependent attenuation coefficient;
wherein an acquired B-mode image of the region of interest and an elasticity coefficient map for the region of interest generated from elasticity data acquired for the region of interest are combined
wherein the acquired B-mode image of the region of interest and an attenuation coefficient map of the region of interest generated from the propagation depth dependent attention coefficients for the region of interest are combined; and
wherein a first combined image and a second combined image are generated, the first combined image representing the acquired B-mode image combined with the elasticity coefficient map, and the second combined image representing the B-mode image combined with the attenuation coefficient map.

2. Method according to claim 1, wherein the transmitted ultrasound pulse is a wide-frequency band pulse or a multifrequency pulse comprising frequency components with frequencies within a predetermined frequency band, and further comprising a step of determining RF signal components with frequencies within a sub range of the predetermined frequency band by filter-bank filtering before step f) of extracting the envelope of the at least one of the RF reception signals,
the envelope extraction being carried out separately for each frequency sub-band component of the RF reception signal,
the logarithmic compression of step g) and the computing the propagation depth dependent attenuation coefficient of step h) being carried out for each frequency sub-band component of the RF reception signal,
i) for each propagation depth of the ultrasound pulse the attenuation coefficient being determined as a mean or median value of the attenuation coefficient calculated for each frequency sub-band component of the RF reception signal.

3. Method according to claim 2, wherein a sequence of several ultrasound pulses is transmitted into the target body and a sequence of reception signals is acquired from the sequence of reflected ultrasound pulses, the step i) being carried out for each of the reception signals of the sequence of reception signals and
k) the propagation depth dependent attenuation coefficient at a propagation depth is computed as the mean or the median value of the attenuation coefficients at the penetration depth of the attenuation coefficients computed from each of the reception signals of the sequence of reception signals.

4. Method according to claim 1, wherein a sequence of several ultrasound pulses is transmitted into the target body and a sequence of reception signals is acquired from a sequence of reflected ultrasound pulses, the steps f) to h) being carried out for each of the reception signals of the sequence of reception signals, and
k) the propagation depth dependent attenuation coefficient at a propagation depth is computed as the mean or the median value of the attenuation coefficients at the penetration depth of the attenuation coefficients computed from each of the reception signals of the sequence of reception signals.

5. Method according to claim 1, wherein before transmitting the shear wave generating pulse of the shear wave generating pulses at least one or a sequence of ultrasound reference pulses is transmitted in the region of interest (2) defined at step b), at least some of reception signals generated by the reflection of the one or more of the reference pulses being used as reception signals for computing the attenuation coefficient at predetermined propagation depths.

6. Method according to claim 5, wherein at least some of the reference pulses are transmitted at least twice, received signals due to the reflected pulse of one of the at least two transmitted reference pulses being used for computing the shear wave velocity while the received signals due to the reflected pulse of the second of the at least two transmitted reference pulses being used for computing the attenuation coefficient.

7. Method according to claim 1, wherein the first combined image comprises the elasticity coefficient map superimposed on the acquired B-mode image, and the second combined image comprises the attenuation coefficient map superimposed on the acquired B-mode image.

8. Method according to claim 1, wherein the first combined image is displayed with respect to the second combined image in a display mode chosen from side by side, overlapped, and alternating, with respect to each other.

9. An ultrasound system for carrying out the method according to claim 1 comprising:

an ultrasound probe configured for transmitting ultrasound pulses into a target body and for receiving reflected ultrasound pulses;

an ultrasound image acquisition section configured to acquire at least ultrasound anatomic images such as B-mode images;

a processing unit configured to calculate attenuation coefficients of tissue crossed by the transmitted ultrasound pulses and the reflected ultrasound pulses, the processing unit being configured to operate as or comprising:

an envelope extractor of the RF reception signals in which the reflected ultrasound pulses are transformed by the ultrasound probe;

a compressor computing a logarithm of the extracted envelope;

the processing unit being configured in carrying out an algorithm for determining a slope of the logarithm of an extracted envelope and computing the attenuation coefficient from the slope.

10. The ultrasound system according to claim 9, wherein the envelope and/or the logarithm of the envelope is determined for frequency sub-ranges of a frequency band of a multifrequency or of a wide frequency range transmission pulse and the attenuation coefficient is computed for each of the frequency sub bands, division in frequency sub bands being carried out by filter-bank filtering.

11. The ultrasound system according to claim 9 further comprising:

an ultrasound shear wave tracking section configured to transmit and receive ultrasound tracking beams in a selected region of interest;

wherein the processing unit is configured to calculate elasticity parameter values in the selected region of interest.

12. The ultrasound system according to claim 9, further comprising:

an ultrasound probe;

an ultrasound transmit wave generator and an ultrasound transmit beamformer;

an ultrasound receive-beamformer;

ultrasound receive signals processing unit for generating ultrasound image data;

a shear wave excitation pulse generator and a shear wave beamformer;

a central control unit comprising:

a memory storing program instructions;

at least one processor that executes the program instructions to:

define a region of interest in the ultrasound image;

generate an acoustic excitation ultrasound pulse directed at an excitation region or point, the acoustic excitation ultrasound pulse being configured to produce a shear wave that has a direction of propagation extending laterally from a direction of propagation of the acoustic excitation ultrasound pulse that is along a direction perpendicular to the direction of transmission of the acoustic excitation ultrasound pulse;

generate ultrasound tracking beams focused along different tracking lines which are at different predetermined laterally staggered distances from one another and from the excitation region or point;

process an ultrasound reflected signal reflected at different tracking focal points distributed along the tracking lines for calculating values of elasticity parameters in the region of interest;

represent an elasticity parameter value distribution in the region of interest by means of an elasticity image, an appearance of pixels of the elasticity image being determined as a function of the elasticity parameter;

scale the elasticity image to be congruent with the region of interest selected on the anatomic image and combining the elasticity image with an anatomic image of the region of interest;

an image display receiving the combined images and displaying the combined images.

* * * * *